United States Patent
Ono et al.

(10) Patent No.: US 7,871,464 B2
(45) Date of Patent: Jan. 18, 2011

(54) ANTHRAPYRIDONE COMPOUND OR SALT THEREOF, MAGENTA INK COMPOSITION AND COLORED PRODUCT

(75) Inventors: Daisuke Ono, Tokyo (JP); Yutaka Ishii, Tokyo (JP); Noriko Kajiura, Tokyo (JP); Hiroyuki Matsumoto, Tokyo (JP)

(73) Assignee: Nippon Kayaku Kabushiki, Tokyo (JP)

( * ) Notice: Subject to any disclaimer, the term of this patent is extended or adjusted under 35 U.S.C. 154(b) by 0 days.

(21) Appl. No.: 12/734,039

(22) PCT Filed: Sep. 1, 2008

(86) PCT No.: PCT/JP2008/065633

§ 371 (c)(1),
(2), (4) Date: Apr. 6, 2010

(87) PCT Pub. No.: WO2009/060654

PCT Pub. Date: May 14, 2009

(65) Prior Publication Data

US 2010/0209678 A1    Aug. 19, 2010

(30) Foreign Application Priority Data

Nov. 6, 2007    (JP) .............................. 2007-288761

(51) Int. Cl.
*C09D 11/02*    (2006.01)
*C09B 5/14*    (2006.01)
*B41J 2/01*    (2006.01)

(52) U.S. Cl. .................. 106/31.47; 546/76; 347/100
(58) Field of Classification Search .............. 106/31.47; 546/76; 347/100; 428/195.1
See application file for complete search history.

(56) References Cited

U.S. PATENT DOCUMENTS

| | | | | |
|---|---|---|---|---|
| 5,367,075 | A * | 11/1994 | Nakamatsu et al. | 546/76 |
| 6,152,969 | A * | 11/2000 | Matsumoto et al. | 546/76 |
| 6,471,760 | B1 | 10/2002 | Matsumoto et al. | |
| 6,843,839 | B2 * | 1/2005 | Kanke et al. | 106/31.47 |
| 7,074,265 | B2 * | 7/2006 | Ikesu et al. | 106/31.47 |
| 7,297,196 | B2 * | 11/2007 | Matsumoto et al. | 106/31.47 |
| 7,691,191 | B2 * | 4/2010 | Matsumoto et al. | 106/31.47 |
| 7,785,411 | B2 * | 8/2010 | Ishii et al. | 106/31.47 |

FOREIGN PATENT DOCUMENTS

| | | |
|---|---|---|
| JP | 2005-206751 A | 8/2005 |
| JP | 2007-314732 A | 12/2007 |
| JP | 2008-202011 A | 9/2008 |
| WO | WO 99/48981 | 9/1999 |

OTHER PUBLICATIONS

International Search Report dated Nov. 18, 2008 in corresponding application (PCT/JP2008/065633).

* cited by examiner

*Primary Examiner*—Helene Klemanski
(74) *Attorney, Agent, or Firm*—Nields, Lemack & Frame, LLC

(57) ABSTRACT

The present invention relates to an anthrapyridone compound represented by the following formula (1):

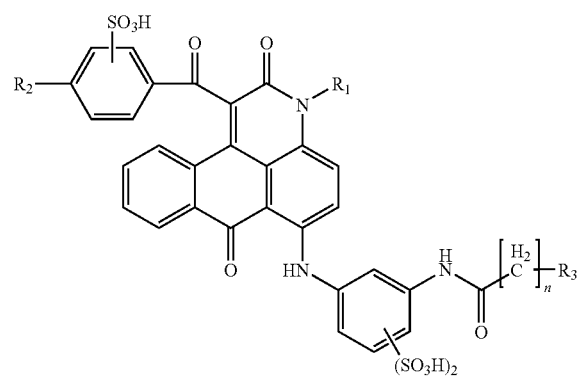

wherein, n represents an integer number of 1 to 3, $R_1$ represents a hydrogen atom, an alkyl group or the like, $R_2$ represents a hydrogen atom or a methoxy group, $R_3$ represents an anilino group having, as a substituent, at least one group selected from the group consisting of sulfo group, a carboxy group, an alkoxy group, a carbamoyl group, an cyano group, an alkyl group, an anilino group, a phenoxy group, an amino group, a hydroxy group and a mercapto group, an unsubstituted anilino group or the like, or a salt thereof, and provides a magenta coloring matter (compound) having high solubility in water and a hue and vividness which are suitable for inkjet recording and being excellent in fastnesses such as light fastness, moisture fastness and ozone gas fastness on recorded matter; and a magenta ink composition containing it.

22 Claims, No Drawings

ANTHRAPYRIDONE COMPOUND OR SALT THEREOF, MAGENTA INK COMPOSITION AND COLORED PRODUCT

TECHNICAL FIELD

The present invention relates to a novel anthrapyridone compound or a salt thereof, a magenta ink composition containing the anthrapyridone compound, and a colored product colored with this composition and the like.

BACKGROUND ART

In the recording method by means of an inkjet printer which is one of the typical methods among various color recording methods, various methods for discharging ink have been developed. In any of the methods, ink droplets are generated and adhered onto various record-receiving materials (such as paper, film and cloth) to perform recording. This has been rapidly prevailing lately and is expected to continue growing remarkably in the future because of features such as quietness without noise generation due to no contact of a recording head with a record-receiving material and as easiness in downsizing, speeding up and colorizing.

Conventionally, as an ink for fountain pens, felt-tip pens or the like and as an ink for inkjet recording, water-based inks where a water-soluble dye is dissolved in an aqueous medium have been used. In these water-based inks, a water-soluble organic solvent is generally added to prevent ink from clogging at a pen tip or an inkjet nozzle. These conventional inks are required to provide recorded images with sufficient density, not to clog at a pen tip or a nozzle, to dry quickly on a record-receiving material, to bleed less, to be excellent in storage stability, and so on. In addition, the images formed are required to have fastnesses such as water fastness, light fastness and moisture fastness.

Meanwhile, images or character information on color displays of computers are generally expressed by subtractive color mixing of 4 primary color inks of yellow (Y), magenta (M), cyan (C) and black (K) for color recording by an ink jet printer. In order that images expressed by additive color mixing of red (R), green (G) and blue (B) on CRT displays and the like is, as faithfully as possible, reproduced with images expressed by subtractive color mixing, it is desired that each of Y, M and C has a hue as close to each standard color as possible and is also vivid. In addition, it is required that ink compositions to be used for them are stable in storage for a long period of time, and that images printed therewith have a high density and said images are excellent in fastnesses such as water fastness, light fastness and gas fastness.

The application of inkjet printers has been widely spread in the fields ranging from small printers for office automation to large printers for industrial use, and therefore fastnesses such as water fastness, moisture fastness, light fastness and gas fastness have been required more than ever.

Water fastness has been largely improved by coating paper surface with inorganic particulates such as porous silica, cation polymer, aluminasol and special ceramic which can absorb coloring matter in ink, together with a PVA resin and the like.

Moisture fastness means durability against a phenomenon that the coloring matter in a record-receiving material bleeds when the colored record-receiving material is stored under an atmosphere of high humidity. Coloring matter bleeding extremely deteriorates image quality in images particularly required to have a high resolution and photo-like image quality, and therefore it is important to reduce such bleeding as far as possible.

As for light fastness, no technique for large improvement thereof has established yet. In particular, many coloring matters for magenta among 4 primary colors of Y, M, C and K originally have low light fastness, and therefore improvement thereof is an important problem.

In addition, there are more opportunities to print pictures at home with recent spread of digital cameras, and image discoloration by oxidizing gases in the air where printed matters obtained are stored is regarded as a problem. The oxidizing gas reacts with coloring matter on or in recorded paper, causing discoloration or fading of the printed image. Among oxidizing gasses, ozone gas is regarded as a main causative matter accelerating color-fading phenomenon of inkjet-recorded images. This phenomenon of discoloration or fading is characteristic of inkjet images, and therefore improvement of ozone gas fastness is also an important problem.

As a magenta coloring matter used in water-based inks for inkjet recording, typical are xanthene-based coloring matters and azo-based coloring matters using H acid (1-amino-8-hydroxy-naphthalene-3,6-disulfonic acid). Xanthene-based ones are very excellent in hue and vividness but very inferior in light fastness. On the other hand, with respect to azo-based coloring matters using H acid, some are good in terms of hue and water fastness, but many are inferior in light fastness and oxidizing gas resistance such as ozone gas fastness and in vividness. In addition, as for this type, a magenta dye relatively excellent in vividness and light fastness has been developed but it still has a low level in light fastness compared with dyes having a different hue such as a cyan dye represented by a copper phthalocyanine-based coloring matter and a yellow dye.

Examples of a magenta coloring matter excellent in vividness and light fastness include an anthrapyridone-based coloring matter (see, for example, Patent Literatures 1 to 12), but a magenta coloring matter satisfying all the requirements of hue, vividness, light fastness, water fastness, oxidizing gas resistance and solution stability has yet to be obtained.

Patent Literature 1: JP H10-306221 A (pp. 1 to 3 and pp. 7 to 18)

Patent Literature 2: JP 2000-109464 A (pp. 1 to 2 and pp. 8 to 12)

Patent Literature 3: JP 2000-169776 A (pp. 1 to 2 and pp 6 to 9)

Patent Literature 4: JP 2000-191660 A (pp. 1 to 3 and pp. 11 to 14)

Patent Literature 5: JP 2000-256587 A (pp. 1 to 3 and pp. 7 to 18)

Patent Literature 6: JP 2001-72884 A (pp. 1 to 2 and pp. 8 to 11)

Patent Literature 7: JP 2001-139836 A (pp. 1 to 2 and pp. 7 to 12)

Patent Literature 8: WO 2004/104108 A1 Booklet (pp. 20 to 36)

Patent Literature 9: JP 2003-192930 A (pp. 1 to 4 and pp. 15 to 18)

Patent Literature 10: JP 2005-8868 A (pp. 1 to 3 and pp. 15 to 22)

Patent Literature 11: JP 2005-314514 A (pp. 1 to 3 and pp. 15 to 20)

Patent Literature 12: WO 2006/075706 A1 Booklet

DISCLOSURE OF THE INVENTION

Problems to Be Solved by the Invention

It is an object of the present invention to provide a magenta coloring matter (compound) having a high solubility in water and a hue and vividness suitable for inkjet recording and allowing recorded matters to be excellent in fastnesses such as light fastness, moisture fastness and ozone gas fastness, and an ink composition containing it.

Means of Solving the Problems

The inventors of the present invention have intensively studied to solve the above problems and found that an anthrapyridone compound shown in a certain formula can solve the above problems, and have completed the present invention. That is, the present invention relates to:

(1) An anthrapyridone compound represented by the following formula (1) or a salt thereof:

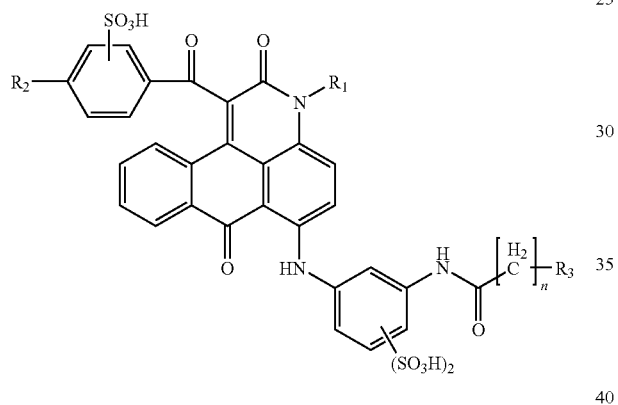

(wherein, n represents an integer number of 1 to 3, $R_1$ represents a hydrogen atom, an alkyl group, a hydroxy lower alkyl group, a cyclohexyl group, a mono- or di-alkylaminoalkyl group, or a cyano lower alkyl group, $R_2$ represents a hydrogen atom or a methoxy group, and $R_3$ represents an unsubstituted anilino group or an anilino group having, as a substituent, at least one group selected from the group consisting of a sulfo group, a carboxy group, an alkoxy group, a carbamoyl group, a cyano group, an alkyl group, an anilino group, a phenoxy group, an amino group, a hydroxy group and a mercapto group;

an unsubstituted mono- or di-alkylamino group or a mono- or di-alkylamino group having, as substituent, at least one group selected from the group consisting of a sulfo group, a carboxy group, an alkoxy group, a carbonyl group, a carbamoyl group, a cyano group, an anilino group, a phenoxy group, an amino group, a monoalkylamino group, a dialkylamino group, a hydroxy group, a mercapto group and a phenyl group;

an unsubstituted phenylthio group or a phenylthio group having, as a substituent, at least one group selected from the group consisting of a sulfo group, a carboxy group, an alkoxy group, a carbonyl group, a carbamoyl group, a cyano group, an alkyl group, an anilino group, a phenoxy group, an amino group, a hydroxy group and a mercapto group;

an unsubstituted alkylthio group or an alkylthio group having, as a substituent, at least one group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group;

a naphthylamino group substituted by a sulfo group or an unsubstituted naphthylamino group;

an unsubstituted phenoxy group or a phenoxy group having, as a substituent, at least one group selected from the group consisting of a sulfo group, a carboxy group, an acetylamino group, an amino group, a hydroxy group, a phenoxy group and a phenyl group;

a hydroxy group; a mercapto group; or an unsubstituted amino group; respectively), (2) The anthrapyridone compound or a salt thereof according to the above (1), which is represented by the following formula (2):

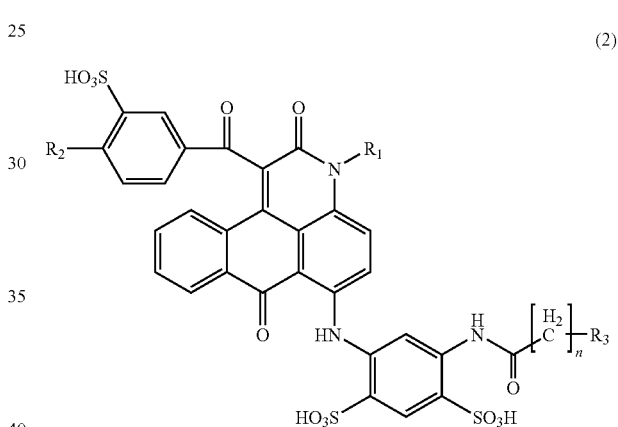

(wherein, n, $R_1$, $R_2$ and $R_3$ have the same meanings as in the formula (1)), (3) The anthrapyridone compound or a salt thereof according to the above (1) or (2), which is represented by the following formula (3):

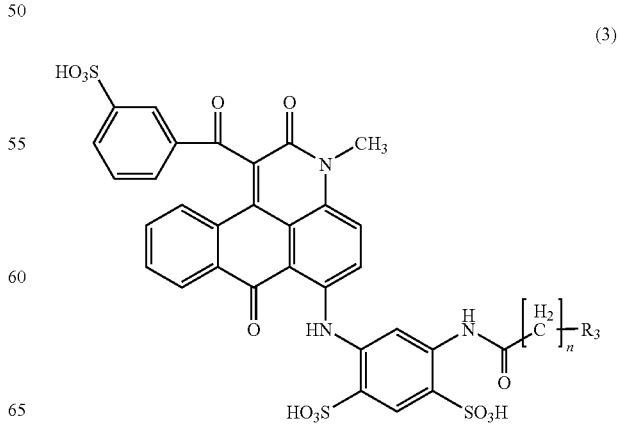

(wherein, n and $R_3$ have the same meanings as in the formula (1)), (4) The anthrapyridone compound or a salt thereof according to the above (3) wherein:

n is an integer number 1 or 2, $R_3$ is an unsubstituted anilino group or an anilino group having, as a substituent, at least one group selected from the group consisting of a sulfo group, a carboxy group, a C1 to C4 alkoxy group, a C1 to C4 alkyl group, an anilino group, a phenoxy group and an amino group;

an unsubstituted mono- or di-C1 to C10 alkylamino group or a mono- or di-C1 to C10 alkylamino group having, as a substituent, at least one group selected from the group consisting of a sulfo group, a carboxy group, a C1 to C4 alkoxy group, an anilino group, a phenoxy group, an amino group, a phenyl group and a hydroxy group;

an unsubstituted phenylthio group or a phenylthio group having, as a substituent, at least one group selected from the group consisting of a sulfo group, a carboxy group, a C1 to C4 alkoxy group, a C1 to C4 alkyl group, an anilino group, a phenoxy group and an amino group;

an unsubstituted alkylthio group or a C1 to C10 alkylthio group having, as a substituent, at least one group selected from the group consisting of a sulfo group, a carboxy group, a C1 to C4 alkoxy group, an anilino group, a phenoxy group and an amino group;

a naphthylamino group substituted by a sulfo group or an unsubstituted naphthylamino group;

an unsubstituted phenoxy group or a phenoxy group having, as a substituent, at least one group selected from the group consisting of a sulfo group, a carboxy group, an acetylamino group, an amino group, a hydroxy group, a phenoxy group and a phenyl group; or a mono- or di-C1 to C4 alkylamino C1 to C4 alkylamino group;

a hydroxy group; a mercapto group; or an amino group, (5) The anthrapyridone compound or a salt thereof according to the above (4), wherein $R_3$ is an unsubstituted anilino group or an anilino group having, as a substituent, a sulfo group or a carboxy group; an unsubstituted mono-C1 to C10 alkylamino group or a mono-C1 to C10 alkylamino group having, as a substituent, a sulfo group, a carboxy group or a phenyl group; an unsubstituted di-C1 to C6 alkylamino group; a phenylthio group substituted by a carboxy group; an unsubstituted C1 to C10 alkylthio group or a C1 to C10 alkylthio group having, as a substituent, a carboxy group or an amino group; or an unsubstituted di-C1 to C4 alkylamino C1 to C4 alkylamino group, (6) The anthrapyridone compound or a salt thereof according to any one of the above (3) to (5), wherein $R_3$ is an unsubstituted anilino group or an anilino group having, as a substituent, a carboxy group; an unsubstituted mono-C1 to C8 alkylamino group or a mono-C1 to C8 alkylamino group having, as a substituent, a sulfo group, a carboxy group or a phenyl group; an unsubstituted di-C1 to C6 alkylamino group; a phenoxy group; a phenylthio group substituted by a sulfo group or a carboxy group; a C1 to C10 alkylthio group substituted by a carboxy group or an unsubstituted C1 to C10 alkylthio group, (7) An ink composition characterized by containing the anthrapyridone compound or a salt thereof according to any one of the above (1) to (6), (8) The ink composition according to the above (7), which contains water and a water-soluble organic solvent, (9) The ink composition according to any one of the above (7) or (8), wherein the content of an inorganic impurity in said compound is 1% by mass or less relative to the total mass of the anthrapyridone compound or a salt thereof according to any one of the above (1) to (6) which is contained in an ink composition as a coloring matter,

(10) The ink composition according to any one of the above (7) to (9), wherein the content of the anthrapyridone compound or a salt thereof according to any one of the above (1) to (6) which is contained in an ink composition as a coloring matter is 0.1 to 20% by mass relative to the total mass of the ink composition,

(11) The ink composition according to the above (7) to (10), which is for inkjet recording,

(12) An inkjet recording method characterized by using the ink composition according to the above (11) as an ink in an inkjet recording method where recording is performed on a record-receiving material by discharging an ink droplet responding to a recording signal,

(13) The inkjet recording method according to the above (12), wherein the record-receiving material is a communication sheet,

(14) The inkjet recording method according to the above (13), wherein the communication sheet has an ink image receiving layer containing a porous white inorganic substance,

(15) A colored product which is colored with the ink composition according to any one of the above (7) to (11),

(16) The colored product according to the above (15), which coloring is conducted by an inkjet printer,

(17) An inkjet printer which comprises a container containing the ink composition according to any one of the above (7) to (10),

(18) An anthrapyridone compound represented by the following formula (4) or a salt thereof:

Formula (4)

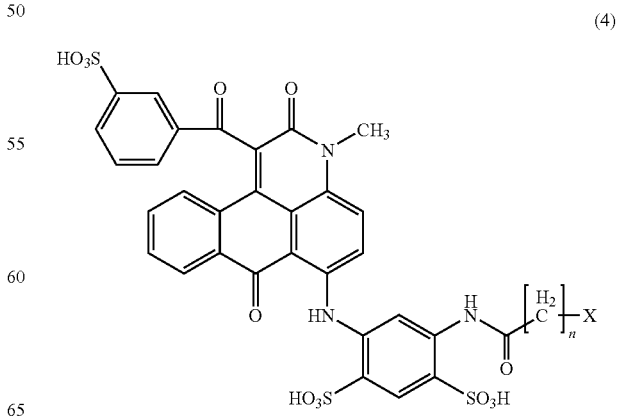

(wherein, n represents an integer number of 1 to 3 and X represents a leaving group),

(19) The anthrapyridone compound or a salt thereof according to the above (18), wherein:

n is an integer number of 1 or 2; and

X is a chlorine atom, a bromine atom or an iodine atom,

(20) The anthrapyridone compound or a salt thereof according to any one of claims 1 to 3, wherein n is an integer number of 1 or 2 and $R_3$ is a carboxy-substituted C3 to C8 alkylamino group,

(21) A method for producing an anthrapyridone compound, which is characterized by reacting an anthrapyridone compound represented by the following formula (10):

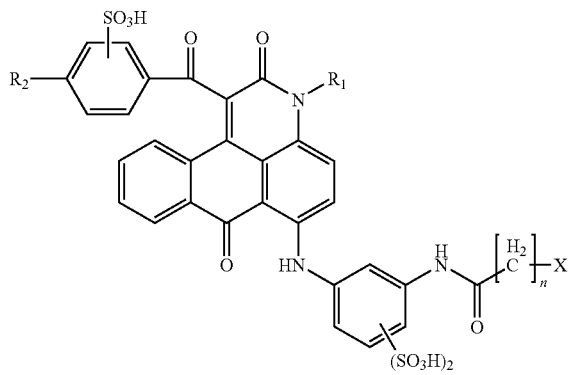

(10)

(wherein, n represents an integer number of 1 to 3, $R_1$ represents a hydrogen atom, an alkyl group, a hydroxy lower alkyl group, a cyclohexyl group, a mono- or di-alkylaminoalkyl group or a cyano lower alkyl group, $R_2$ represents a hydrogen atom or a methoxy group, and X represents a leaving group)

or a salt thereof with a compound represented by

Formula $R_3$—H (wherein, $R_3$ represents;

an unsubstituted anilino group or an anilino group having, as a substituent, a group selected from the group consisting of a sulfo group, a carboxy group, an alkoxy group, a carbamoyl group, a cyano group, an alkyl group, an anilino group, a phenoxy group, an amino group, a hydroxy group and a mercapto group;

an unsubstituted mono- or di-alkylamino group or a mono- or di-alkylamino group having, as a substituent, a group selected from the group consisting of a sulfo group, a carboxy group, an alkoxy group, a carbonyl group, a carbamoyl group, a cyano group, an anilino group, a phenoxy group, an amino group, a monoalkylamino group, a dialkylamino group, a hydroxy group, a mercapto group and a phenyl group;

an unsubstituted phenylthio group or a phenylthio group having, as a substituent, a group selected from the group consisting of a sulfo group, a carboxy group, an alkoxy group, a carbonyl group, a carbamoyl group, a cyano group, an alkyl group, an anilino group, a phenoxy group, an amino group, a hydroxy group and a mercapto group;

an unsubstituted alkylthio group or an alkylthio group having, as a substituent, a group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group;

a naphthylamino group substituted by a sulfo group or an unsubstituted naphthylamino group;

an unsubstituted phenoxy group or a phenoxy group having, as a substituent, a group selected from the group consisting of a sulfo group, a carboxy group, an acetylamino group, an amino group, a hydroxy group, a phenoxy group and a phenyl group;

a hydroxy group; a mercapto group; or an unsubstituted amino group), and which is represented by the following formula (1) or a salt thereof:

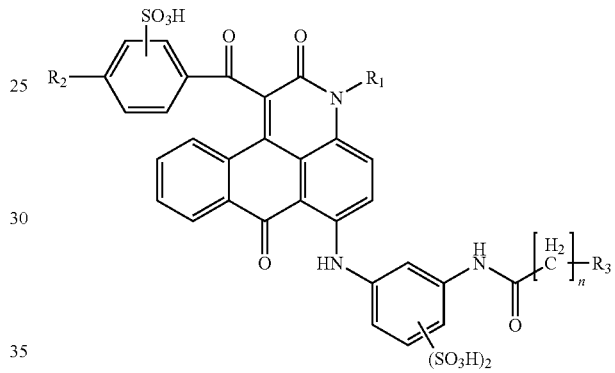

(1)

(wherein, n, $R_1$, $R_2$ and $R_3$ have the same meanings as the above),

(22) An anthrapyridone compound represented by the following formula (113) or a salt thereof:

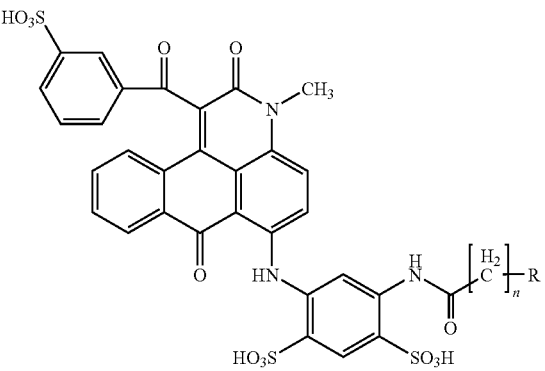

(113)

(wherein, n represents an integer number of 1 to 3, and R represents an unsubstituted anilino group or an anilino group having, as a substituent, a carboxy group;

an unsubstituted mono-C1 to C10 alkylamino group or a mono-C1 to C8 alkylamino group having, as a substituent, a sulfo group, a carboxy group or a phenyl group;

an unsubstituted di-C1 to C6 alkylamino group; a phenoxy group; a phenylthio group substituted by a sulfo group or a carboxy group; a C1 to C10 alkylthio group substituted by a carboxy group or an unsubstituted C1 to C10 alkylthio group; or a halogen atom).

EFFECT OF THE INVENTION

The anthrapyridone compound represented by the above formula (1) of the present invention or a salt thereof has characteristics of having a very vivid and highly bright hue on an inkjet recording paper, excellent water-solubility and good filterability through a membrane filter in the production process of ink composition. In addition, the ink composition of the present invention containing this compound is free from solid precipitation, change in physical properties, color change and the like after storage for a long period of time, and therefore has good storage stability. And a printed matter using the anthrapyridone compound of the present invention or a salt thereof as a magenta ink for inkjet recording has an ideal magenta hue without selecting a record-receiving material (paper, film and the like). Further, the magenta ink composition of the present invention can also allow faithfully reproducing photo-like color images on paper. Furthermore, even when recording is performed on a record-receiving material whose surface is coated with inorganic particles, such as inkjet special paper (film) for photo image quality, it is good in fastnesses such as light fastness, ozone fastness and moisture fastness and the long-term storage stability of photo-like recorded images is excellent. Therefore, the anthrapyridone compound represented by the above formula (1) or a salt thereof is extremely useful as an ink coloring matter for inkjet recording.

BEST MODE FOR CARRYING OUT THE INVENTION

The present invention will be specifically explained. In this context, unless otherwise specifically noted in the present invention, an acidic functional group such as a sulfo group and a carboxy group is shown in free acid form. In addition, "anthrapyridone compound or a salt thereof" is described hereinafter, for convenience, as "anthrapyridone compound" including the meaning of said compound or a salt thereof, because it is troublesome to describe them. The descriptions of "compound represented by the formula (1)" and "compound of the present invention" also mean just like them to include a salt thereof, respectively.

In the present description, unless otherwise specifically noted, "alkyl" may be any of straight-chain, branched and cyclic. It is preferably straight-chain or branched and more preferably straight-chain.

In addition, said alkyl represents, except when specifically noted, alkyl having 1 to 10 carbon atoms, for example, methyl, ethyl, n-propyl, isopropyl, cyclopropyl, n-butyl, isobutyl, sec-butyl, tert-butyl, n-pentyl, isopentyl, n-hexyl, cyclohexyl, n-heptyl, n-octyl, n-nonyl, n-decyl and the like.

With respect to "acyl" and "alkoxy" in the present description, the alkyl group moiety in these groups has, unless otherwise specifically noted, the same meaning as that of the above alkyl.

Further, "lower alkyl" in the present description can include, unless otherwise specifically noted, C1 to C6 alkyl and preferably C1 to C4 alkyl in the above alkyls, and preferable specific examples thereof can include methyl, ethyl, propyl or butyl.

The anthrapyridone compound of the present invention is represented by the above formula (1).

n in the formula (1) represents the number of methylene group in the formula (1) and an integer number of 1 to 3. Preferably, n is an integer number of 1 or 2, and most preferably 1.

In the formula (1), $R_1$ represents a hydrogen atom, an alkyl group, a hydroxy lower alkyl group, a cyclohexyl group, a mono- or di-alkylaminoalkyl group or a cyano lower alkyl group. In this regard, the hydroxy lower alkyl group in $R_1$ includes, for example, hydroxyethyl, hydroxypropyl and the like, the monoalkylaminoalkyl group includes, for example, methylaminopropyl, ethylaminopropyl and the like, the dialkylaminoalkyl includes, for example, dimethylaminopropyl, diethylaminoethyl and the like, and the cyano lower alkyl group includes, for example, cyanoethyl, cyanopropyl and the like.

Preferable $R_1$ includes a hydrogen atom and a lower alkyl group, a hydrogen atom or methyl is more preferably, and methyl is particularly preferable.

In the formula (1), $R_2$ represents a hydrogen atom or a methoxy group and a hydrogen atom is more preferable.

$R_3$ in the formula (1) represents a group explained in the above formula (1). Hereinafter, $R_3$ will be specifically explained When $R_3$ in the formula (1) is an anilino group (substituted anilino group) having, as a substituent, at least one group selected from the group consisting of a sulfo group, a carboxy group, an alkoxy group, an alkyl group, an anilino group, a phenoxy group and an amino group, the number of substituent on the anilino group is usually 1 to 4, preferably 1 to 3 and more preferably 1 or 2.

Specific examples of said substituted anilino group include, for example, sulfo-substituted anilino such as 2-sulfoanilino, 3-sulfoanilino, 4-sulfoanilino and 2,5-disulfoanilino; carboxy-substituted anilino such as 2-carboxyanilino, 4-carboxyanilino and 3,5-dicarboxyanilino; (C1 to C3)alkoxy-substituted anilino such as 4-methoxyanilino; alkyl-substituted anilino such as 4-butylanilino; anilino- and sulfo-substituted anilino such as 4-anilino-3-sulfoanilino; phenoxy-substituted anilino such as 4-phenoxyanilino; amino-substituted anilino such as 4-aminoanilino; and the like.

In addition, specific examples thereof further include a sulfoanilino group substituted by a methyl group, a methoxy group or a carboxy group and a carboxy-substituted hydroxyanilino group.

When $R_3$ in the formula (1) is a sulfoanilino group having, as a substituent, a methyl group, a methoxy group or a carboxy group, the number of substituent any one of the methyl group, the methoxy group or the carboxy group is preferably 1 or 2 and more preferably 1. Specific examples thereof include methyl-substituted sulfoanilino such as 4-methyl-2-sulfoanilino and 2-methyl-4-sulfoanilino; methoxy-substituted sulfoanilino such as 4-methoxy-2-sulfoanilino; and carboxy-substituted sulfoanilino such as 2-carboxy-5-sulfoanilino and 2-carboxy-4-sulfoanilino.

When $R_3$ in the formula (1) is carboxy-substituted hydroxyanilino group, the number of the carboxy group is preferably 1 or 2 and more preferably 1. Specific examples thereof include 3-carboxy-4-hydroxyanilino and the like.

Said substituted anilino group or unsubstituted anilino group in $R_3$ including these groups is preferably an anilino group having, as a substituent, at least one group selected from the group consisting of a sulfo group, a carboxy group, a C1 to C4 alkoxy group, a C1 to C4 alkyl group, an anilino group, a phenoxy group and an amino group or an unsubstituted anilino group, more preferably a sulfo-substituted or carboxy-substituted anilino group or an unsubstituted anilino group, and further preferably a carboxy-substituted anilino group or an unsubstituted anilino group.

In addition, optionally, the substituted anilino group in $R_3$ is preferably a sulfoanilino group substituted by a methyl group, a methoxy group or a carboxy group; a carboxy-substituted hydroxyanilino group; or the like.

When $R_3$ is a mono- or di-alkylamino group having, as a substituent, at least one group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group or an unsubstituted mono- or di-alkylamino group, said alkyl moiety is preferably a C1 to C10 alkyl group as described above.

The number of substituent on the alkyl group of said mono- or di-alkylamino group is limited in the range that it can be substituted, usually 1 to 4, preferably 1 to 3 and more preferably 1 or 2.

Specific examples of unsubstituted or substituted alkyl in said mono- or di-alkylamino group include, for example, unsubstituted straight-chain alkyl such as methyl, ethyl, propyl, butyl, pentyl, hexyl, heptyl, octyl, nonyl and decyl; unsubstituted branched alkyl such as 2-ethylhexyl; unsubstituted cyclic alkyl such as cyclohexyl; sulfo-substituted alkyl such as 2-sulfoethylamino; carboxy-substituted alkyl such as carboxymethyl, 2-carboxyethyl, 1,2-dicarboxyethyl, 1,3-dicarboxypropyl and 5-carboxypentyl; alkoxy-substituted alkyl such as 3-ethoxypropyl; carbonyl-substituted alkyl such as 3-oxobutyl; carbamoyl-substituted alkyl such as 2-aminocarbonylethyl; cyano-substituted alkyl such as 3-cyanopropyl; anilino-substituted alkyl such as 2-phenylaminoethyl; phenoxy-substituted alkyl such as 2-phenoxyethyl; amino-substituted alkyl such as N-(3-hydroxypropyl)aminoethyl, 2-methylaminoethyl, 3-methylaminopropyl, 3-ethylaminopropyl, 3-(N,N-diethylamino)propylamino and 2-(N,N-diethylamino)ethylamino; hydroxy group-substituted alkyl such as 2-hydroxyethyl; mercapto group-substituted alkyl such as 2-thioethyl; phenyl-substituted alkyl such as benzyl; and the like. In this regard, in the case of a monoalkylaminoalkylamino group, the range of said alkyl is usually C1 to C10, preferably C1 to C6 and more preferably C1 to C4. In addition, in the case of a dialkylaminoalkylamino group, it may independently have two moieties of "monoalkyl" in the above monoalkylaminoalkylamino group.

Said mono- or di-alkylamino group in $R_3$ is preferably a mono- or di-alkylamino group having, as a substituent, 1 or 2 and preferably 1 group selected from the group consisting of a sulfo group, a carboxy group, a C1 to C4 alkoxy group, an anilino group, a phenoxy group, an amino group, a mono- or di-alkylamino group, a phenyl group and a hydroxy group or an unsubstituted mono- or di-alkylamino group.

The substituted or unsubstituted alkyl in said monoalkylamino group is preferably sulfo-substituted, carboxy-substituted or phenyl-substituted alkyl or unsubstituted alkyl. Said monoalkylamino group is preferably a mono-C1 to C10 alkylamino group having, as a substituent, a sulfo group, a carboxy group or a phenyl group or an unsubstituted mono-C1 to C10 alkylamino group, more preferably a mono-C1 to C8 alkylamino group having, as a substituent, a sulfo group, a carboxy group or a phenyl group or an unsubstituted mono-C1 to C8 alkylamino group, and further preferably a mono-C3 to C8 alkylamino group having, as a substituent, a sulfo group, a carboxy group or a phenyl group or an unsubstituted mono-C1 to C6 alkylamino group. Most preferable is a carboxy C3 to C8 alkylamino group.

When $R_3$ is said dialkylamino group, said alkyl group is preferably a C1 to C6 alkyl group and more preferably a C1 to C4 alkyl group. Specific examples of said dialkylamino group can include an amino group substituted by a group independently selected from, for example, the specific examples of the above alkyl, and it can preferably include unsubstituted dialkylamino such as dimethylamino, diethylamino, dipropylamino and dibutylamino; bis(carboxy-substituted alkyl) amino such as bis(carboxymethyl)amino; bis(hydroxy-substituted alkyl)amino such as bis(2-hydroxyethyl)amino; and the like. More preferable is unsubstituted dialkylamino. Said dialkylamino group is preferably unsubstituted di-C1 to C6 alkylamino and more preferably unsubstituted di-C1 to C4 alkylamino.

When $R_3$ is a phenylthio group having, as a substituent, at least one group selected from the group consisting of a sulfo group, a carboxy group, an alkoxy group, a carbonyl group, a carbamoyl group, a cyano group, an alkyl group, an anilino group, a phenoxy group, an amino group, a hydroxy group and a mercapto group, specific examples thereof include, for example, sulfo-substituted phenylthio such as 4-sulfophenylthio; carboxy-substituted phenylthio such as 4-carboxyphenylthio and 3,5-dicarboxyphenylthio; alkoxy-substituted phenylthio such as 3-ethoxyphenylthio; carbonyl-substituted phenylthio such as acetylphenylthio; carbamoyl-substituted phenylthio such as 3-aminocarbonylphenylthio; cyano-substituted phenylthio such as 3-cyanophenylthio; alkyl-substituted phenylthio such as 4-ethylphenylthio; anilino-substituted phenylthio such as 3-phenylaminophenylthio; phenylthio substituted by phenoxy or carboxy-substituted phenoxy such as 4-phenoxyphenylthio and 4-(4-carboxyphenoxy)phenylthio; amino-substituted phenylthio such as 3-aminophenylthio; hydroxy group-substituted phenylthio such as 4-hydroxyphenylthio; mercapto group-substituted phenylthio such as 4-mercaptophenylthio; phenylthio substituted by an amino group where one of the hydrogen atoms is substituted by an acyl group, such as 4-acetylaminophenylthio; and the like. The number of substituent on said phenylthio group is usually 1 to 4, preferably 1 to 3 and more preferably 1 or 2.

Among these groups, a phenylthio group substituted by a sulfo group or a carboxy group is preferable and more preferable is a carboxy-substituted phenylthio group.

When $R_3$ is an alkylthio group having, as a substituent, at least one group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group or an unsubstituted alkylthio group, said alkyl moiety is preferable a C1 to C10 alkyl group.

The number of substituent on said alkylthio group is not limited, but usually 1 to 4, preferably 1 to 3, more preferably 1 or 2 and further preferably 1.

Specific examples of said alkylthio group include, for example, straight-chain alkylthio such as methylthio, ethylthio, propylthio, butylthio, pentylthio, hexylthio, heptylthio, octylthio, nonylthio and decylthio; branched alkylthio such as 2-methylbutylthio and 2-ethylhexylthio; cyclic alkylthio such as cyclohexylthio; sulfo-substituted alkylthio such as 2-sulfoethylthio; carboxy-substituted alkylthio such as 2-carboxyethylthio, 1,2-dicarboxyethylthio and 1,3-dicarboxypropylthio; alkoxy-substituted alkylthio such as 2-methoxyethylthio; carbonyl-substituted alkylthio such as 3-oxobutylthio; carbamoyl-substituted alkylthio such as 2-aminocarbonylethylthio; cyano-substituted alkylthio such as 5-cyanopentylthio; anilino-substituted alkylthio such as 2-phenylaminoethylthio; phenoxy-substituted alkylthio such as phenoxyethylthio; amino-substituted alkylthio where unsubstituted or one of the hydrogen atoms on the amino group is substituted by an alkyl group, such as amino-substituted ethylthio or N-methylaminoethylthio; hydroxy-substituted alkylthio such as 2-hydroxyethylthio; mercapto-substituted alkylthio such as 4-mercaptobutylthio; phenyl-substituted alkylthio such as 2-phenylethylthio; and the like.

Said alkylthio group is preferably C1 to C10 alkylthio substituted by a group selected from the group consisting of a sulfo group, a carboxy group, a C1 to C4 alkoxy group, an anilino group, a phenoxy group and an amino group or unsubstituted alkylthio (preferably, unsubstituted C1 to C10 alkylthio), more preferably, carboxy-substituted, amino-substituted or unsubstituted C1 to C10 alkylthio, and further preferably carboxy-substituted or unsubstituted C1 to C10 alkylthio.

When $R_3$ is a naphthylamino group substituted by a sulfo group, the number of the sulfo group is usually 1 to 5, preferably 1 to 4 and more preferably 1 to 3.

When $R_3$ is a naphthylamino group substituted by a sulfo group or an unsubstituted naphthylamino group, specific examples thereof include, for example unsubstituted naphthylamino such as 1-naphthylamino; monosulfonaphthylamino such as 4-sulfo-1-naphthylamino, 5-sulfo-1-naphthylamino, 5-sulfo-2-naphthylamino, 6-sulfo-1-naphthylamino and 7-sulfo-1-naphthylamino; disulfonaphthylamino such as 4,8-disulfo-2-naphthylamino, 3,8-disulfo-1-naphthylamino and 3,6-disulfo-1-naphthylamino; trisulfonaphthylamino such as 3,6,8-trisulfo-2-naphthylamino, 4,6,8-trisulfo-2-naphthylamino and 3,6,8-trisulfo-1-naphthylamino; and the like.

When $R_3$ is a phenoxy group (substituted phenoxy group) having, as a substituent, at least one group selected from the group consisting of a sulfo group, a carboxy group, an acetylamino group, an amino group, a hydroxy group, a phenoxy group and a phenyl group, the number of substituent is usually 1 to 3 and preferably 1 or 2.

Specific examples thereof include, for example, sulfo-substituted phenoxy such as 4-sulfophenoxy; carboxy-substituted phenoxy such as 4-carboxyphenoxy and 3,5-dicarboxyphenoxy; acetylamino-substituted phenoxy such as 4-acetylaminophenoxy; amino-substituted phenoxy such as 2-aminophenoxy; hydroxy group-substituted phenoxy such as 4-hydroxyphenoxy; phenoxy substituted by phenoxy or carboxy-substituted phenoxy, such as 4-phenoxyphenoxy or 4-(4-carboxyphenoxy)phenoxy; phenyl-substituted phenoxy such as 4-phenylphenoxy; and the like.

When $R_3$ is said substituted phenoxy group or unsubstituted phenoxy group, preferable is an unsubstituted phenoxy group.

When $R_3$ is a monoalkylaminoalkylamino group, the range of said alkyl is usually C1 to C10, preferably C1 to C6 and more preferably C1 to C4.

Specific examples of said monoalkylaminoalkylamino group include, for example, 2-methylaminoethylamino, 3-methylaminopropylamino, 3-ethylaminopropylamino and the like.

When $R_3$ is a dialkylaminoalkylamino group, it may independently have two moieties of "monoalkyl" in the above monoalkylaminoalkylamino group. The range of said alkyl is also the same including the preferable ones. Specific examples of said dialkylaminoalkylamino group include, for example, 3-(N,N-diethylamino)propylamino, 2-(N,N-diethylamino)ethylamino and the like.

It is preferred that $R_3$ is selected from the group consisting of the groups listed as a preferable group for each group in the above.

Preferable $R_3$ includes an anilino group substituted by a group selected from the group consisting of a sulfo group, a carboxy group, a C1 to C4 alkoxy group, a C1 to C4 alkyl group, an anilino group, a phenoxy group and an amino group, or an unsubstituted anilino group; a mono- or di-C1 to C10 alkylamino group substituted by a group selected from the group consisting of a sulfo group, a carboxy group, a C1 to C4 alkoxy group, an anilino group, a phenoxy group, an amino group, a phenyl group and a hydroxy group or an unsubstituted mono- or di-C1 to C10 alkylamino group; a phenylthio group substituted by a group selected from the group consisting of a sulfo group, a carboxy group, a C1 to C4 alkoxy group, a C1 to C4 alkyl group, an anilino group, a phenoxy group and an amino group, or an unsubstituted phenylthio group; a C1 to C10 alkylthio group substituted by a group selected from the group consisting of a sulfo group, a carboxy group, a C1 to C4 alkoxy group, an anilino group, a phenoxy group and an amino group, or an unsubstituted alkylthio group (preferably unsubstituted C1 to C10 alkyl group); a sulfoanilino group substituted by a methyl group, a methoxy group or a carboxy group; a carboxy-substituted hydroxyanilino group; a naphthylamino group substituted by a sulfo group, or an unsubstituted naphthylamino group; a phenoxy group substituted by a group selected from the group consisting of a sulfo group, a carboxy group, an acetylamino group, an amino group, a hydroxy group, a phenoxy group and a phenyl group, or an unsubstituted phenoxy group; a mono- or di-C1 to C4 alkylamino C1 to C4 alkylamino group; a hydroxy group; a mercapto group; and an amino group.

More preferable $R_3$ includes an anilino group substituted by a sulfo group or a carboxy group, or unsubstituted anilino group; a mono-C1 to C10 alkylamino group substituted by a sulfo group, a carboxy group or a phenyl group, or an unsubstituted mono-C1 to C10 alkylamino group; an unsubstituted di-C1 to C6 alkylamino group; a phenylthio group substituted by a carboxy group; a C1 to C10 alkylthio group substituted by a carboxy group or an amino group, or unsubstituted C1 to C10 alkylthio group; and an unsubstituted di-C1 to C4 alkylamino C1 to C4 alkylamino group.

Further preferable $R_3$ includes an anilino group substituted by a carboxy group, or an unsubstituted anilino group; a mono-C1 to C8 alkylamino group substituted by a sulfo group, a carboxy group or a phenyl group, or an unsubstituted mono-C1 to C8 alkylamino group; an unsubstituted di-C1 to C6 alkylamino group; a phenoxy group; a phenylthio group substituted by a sulfo group or a carboxy group; a C1 to C10 alkylthio group substituted by a carboxy group and an unsubstituted C1 to C10 alkylthio group, and among them more preferable are a mono-C1 to C8 alkylamino group substituted by a sulfo group, a carboxy group or a phenyl group, or an unsubstituted mono-C1 to C8 alkylamino group.

Most preferable $R_3$ can include a carboxy-substituted C3 to C8 alkylamino group.

With respect to the above all groups represented by the above $R_1$ to $R_3$ and the substituents therein, when these groups have a hydrogen atom, said hydrogen atom may be substituted by a group other than a hydrogen atom as long as it can achieve the effect of the Invention, but usually it is preferably unsubstituted.

The compound represented by the following formula (10):

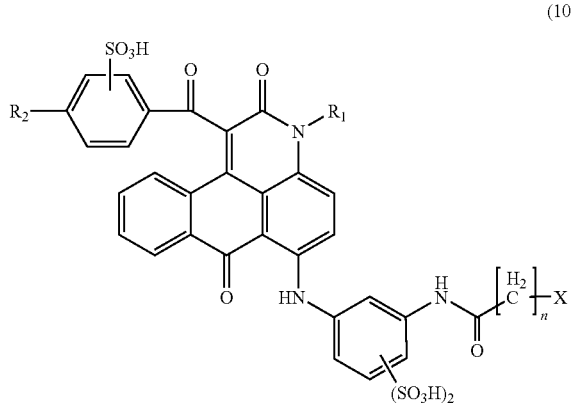

(10)

(wherein, n, $R_1$ and $R_2$ have the same meanings as in the above formula (1), and X represents a leaving group)

which is an intermediate in the method for producing the above formula (1) described later is useful as a coloring matter for ink or the like as well as the compound of the above formula (1), and also important as an intermediate for synthesis of the compounds of the formulas (1) to (3).

The compound of the above formula (4) is a preferable compound of the above formula (10), useful as a coloring matter for ink or the like, and also one of the preferable ones as an intermediate for synthesis of the compounds of the above formulas (1) to (3).

In the formula (10) or the formula (4), n is preferably 1 or 2.

X in the compound represented by the formula (10) or the formula (4) is not particularly limited as long as it can be used as a leaving group, and it includes a halogen atom such as a chlorine atom, a bromine atom and an iodine atom; an alkylsulfonyloxy group such as a methanesulfonyloxy group; a halogenoalkylsulfonyloxy group such as a trifluoromethanesulfonyloxy group; a phenylsulfonyloxy group or a substituted phenylsulfonyloxy group such as a benzenesulfonyloxy group and a toluenesulfonyloxy group; and the like. Said various sulfonyloxy groups may be, as it is, used as a leaving group. Otherwise, they may be used for synthesis reaction of the compound of the above formula (1) by substituting a sulfonyloxy group to a halogen atom in the reaction system during reaction following the conventional manner using a halogenating agent such as halogenated alkali metals, for example, halogenated sodium such as sodium iodide or sodium bromide; halogenated potassium such as potassium iodide or potassium bromide; and halogenated lithium such as lithium iodide or lithium bromide. When X is used as a leaving group, preferable X is a halogen atom.

When the compound represented by the above formula (10) or the above formula (4) is used as a synthesis intermediate for the compound represented by the above formula (1), the leaving group represented by X is not particularly limited to the above as long as it has sufficient reactivity for nucleophilic substitution reaction.

When said compound is used as a coloring matter contained in an ink composition or the like as the anthrapyridone compound of the present invention, it is advisable to select a relatively stable one among leaving groups in view of storage stability and the like. In this case, it is preferred that X is a halogen atom, particularly a chlorine atom.

With respect to all the groups and substituents in the above formula (1), a compound as a combination of preferable ones is more preferable, and a compound as a combination of more preferable compounds is further preferable. The same holds for a combination of further preferable ones and particularly preferable ones. One of the preferable compounds of the formula (1) can include the compound of the formula (2), and one of the more preferable compounds include the compound of the formula (3).

More specifically, a preferable anthrapyridone compound of the present invention includes a compound where in the above formula (1) and preferably in the above formula (2), $R_1$ is a hydrogen atom or a lower alkyl group, more preferably a hydrogen atom or a methyl group and further preferably a methyl group and $R_2$ is a hydrogen atom. Therefore, the compound represented by the above formula (3) is one of the preferable anthrapyridone compounds of the present invention In these preferable compounds, a compound as a combination of "preferable $R_3$", "more preferable $R_3$", "further preferable $R_3$" or "most preferable $R_3$" is further one of more preferable anthrapyridone compounds of the present invention.

In addition, in the above preferable compounds, a compound where n is an integer number of 1 or 2 is further one of more preferable anthrapyridone compounds of the present invention.

Further, a compound where in the above formula (1), preferably in the formula (2) and more preferably in the formula (3), n is an integer number of 1 or 2, and $R_3$ is "preferable $R_3$", "more preferable $R_3$", "further preferable $R_3$" or "most preferable $R_3$" is one of preferable anthrapyridone compounds of the present invention. Furthermore, in these preferable compounds of the formula (1) or (2), a compound where $R_1$ is a hydrogen atom or a lower alkyl group, more preferably a hydrogen atom or a methyl group, and further preferably a methyl group, and $R_2$ is a hydrogen atom is one of more preferable compounds.

A further preferable anthrapyridone compound of the present invention is a compound where in the formula (3), n is an integer number of 1 or 2, and $R_3$ is a mono-C1 to C8 alkylamino group substituted by a sulfo group, a carboxy group or a phenyl group or an unsubstituted mono-C1 to C8 alkylamino group, and most preferable is a compound where n is 1 and $R_3$ is a carboxy-substituted mono-C3 to C8 alkylamino group.

In addition, in the present invention, an anthrapyridone compound represented by the following formula (113):

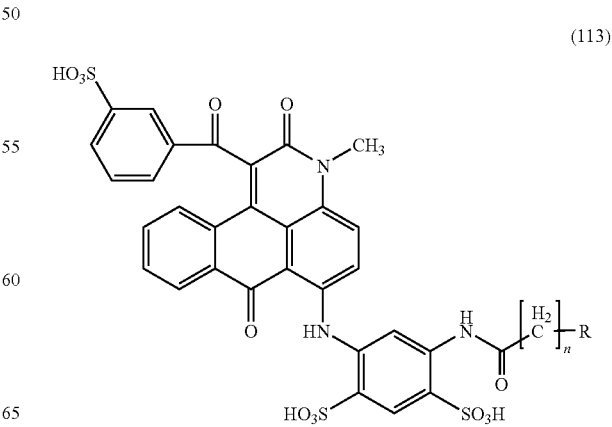

(113)

(wherein, n is an integer number of 1 to 3, R is an unsubstituted anilino group or an anilino group having, as a substituent, a carboxy group; an unsubstituted mono-C1 to C10 alkylamino group or a mono-C1 to C8 alkylamino group having, as a substituent, a sulfo group, a carboxy group or a phenyl group; an unsubstituted di-C1 to C6 alkylamino group; a phenoxy group; a phenylthio group substituted by a sulfo group or a carboxy group; a C1 to C10 alkylthio group substituted by a carboxy group or an unsubstituted C1 to C10 alkylthio group; or a halogen atom) or a salt thereof is also one of the preferable compounds.

A preferable compound of the formula (113) is a compound where R is a carboxy-substituted C1 to C8 alkylamino group (preferably carboxy-substituted C3 to C8 alkylamino group) or a halogen atom. In this preferable compound, n is more preferably 1 or 2 and n is further preferably 1.

The salt of the compound represented by the above formula (1) is a salt with an inorganic or organic base. Among them, specific examples of the inorganic salt include alkali metal salts, alkali earth metal salts and ammonium salts, and preferable inorganic salts are salts of lithium, sodium and potassium and ammonium salts. On the other hand, the salt with an organic base includes, for example, salts with quaternary ammonium ion (organic ammonium salts) represented by the following formula (5). However, the salt with an inorganic or organic base is not limited these. In addition, free acid and each salt may be a mixture, and any combination may be used, for example, a mixture of a sodium salt and an inorganic or organic ammonium salt, a mixture of a free acid and a sodium salt, a mixture of an lithium salt, a sodium salt and an inorganic or organic ammonium salt, and the like. There are cases where the physical property value such as solubility varies depending on the kind of salt, and it is also possible to obtain a mixture having physical properties suitable for the intended purpose by, according to necessity, appropriately selecting the kind of salt and by changing the rate when containing a plural kinds of salts.

Formula (5)

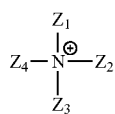

(5)

(wherein, each of $Z_1$ to $Z_4$ independently represents a hydrogen atom, an alkyl group, a hydroxyalkyl group or a hydroxyalkoxyalkyl group, and at least one of $Z_1$ to $Z_4$ represents a group other than a hydrogen atom.)

Examples of the alkyl group for $Z_1$ to $Z_4$ in the formula (5) include methyl, ethyl and the like, examples of the hydroxyalkyl group include hydroxymethyl, 2-hydroxyethyl, 3-hydroxypropyl, 2-hydroxypropyl, 4-hydroxybutyl, 3-hydroxybutyl, 2-hydroxybutyl and the like, and in addition, examples of the hydroxyalkoxyalkyl group include hydroxyethoxymethyl, 2-hydroxyethoxyethyl, 3-hydroxyethoxypropyl, 3-hydroxyethoxybutyl, 2-hydroxyethoxybutyl and the like.

Preferable bases to form the above salt include, for example, sodium, potassium, lithium, monoethanolamine, diethanolamine, triethanolamine, monoisopropanolamine, diisopropanolamine, triisopropanolamine and ammonium and the like. Among them, particularly preferable are lithium salts, ammonium salts and sodium salts.

As for the above salt, for example, a sodium salt can be obtained as a wet cake by adding sodium chloride to the reaction liquid or an aqueous solution dissolving a (wet) cake, a dried form or the like of an intended product, followed by salting out and filtration. In addition, it is possible to obtain in free acid form (or partially sodium salt) by that the wet cake is again dissolved in water and then the pH is adjusted to 1 to 2 by adding hydrochloric acid to obtain a solid which is then filtered. Further, by dissolving the wet cake of free acid in water and then by adding, for example, potassium hydroxide, lithium hydroxide, ammonia water and the compound represented by the formula (1) for alkalization, each corresponding potassium salt, lithium salt, ammonium salt and a salt with an organic base can be obtained.

Specific examples of the anthrapyridone compound represented by the formula (1) of the present invention will be shown in the following table 1, but it is not particularly limited to these.

TABLE 1

| Compound No. | R1 | R2 | n | R3 |
|---|---|---|---|---|
| 1 | Methyl | H | 1 | Butylamino |
| 2 | Methyl | H | 1 | 5-Carboxypentylamino |
| 3 | Methyl | H | 1 | 2-Carboxyethylthio |
| 4 | Methyl | H | 1 | 2-Carboxyphenylthio |
| 5 | Methyl | H | 1 | Benzylamino |
| 6 | Methyl | H | 1 | Anilino |
| 7 | Methyl | H | 1 | Octylthio |
| 8 | Methyl | H | 1 | Hexylamino |
| 9 | Methyl | H | 2 | 2-Carboxyphenylthio |
| 10 | Methyl | H | 1 | Diethylamino |
| 11 | Methyl | H | 1 | Diisopropylamino |
| 12 | Methyl | H | 2 | 5-Carboxypentylamino |
| 13 | Methyl | H | 2 | Butylamino |
| 14 | Methyl | H | 1 | Dibutylamino |
| 15 | Methyl | H | 1 | 3-Carboxypropylamino |
| 16 | Methyl | H | 1 | N,N-Bis(carboxymethyl)amino |
| 17 | Methyl | H | 1 | Octylamino |
| 18 | Methyl | H | 1 | 2-Ethylhexylamino |
| 19 | Methyl | H | 1 | 2-Carboxyanilino |
| 20 | Methyl | H | 1 | Dimethylaminopropylamino |
| 21 | Methyl | H | 1 | 2-Aminoethylthio |
| 22 | Methyl | H | 1 | Carboxymethylamino |
| 23 | Methyl | H | 2 | Carboxymethylamino |
| 24 | Methyl | H | 1 | 2-Sulfoethylamino |
| 25 | Methyl | H | 1 | 3-Sulfoanilino |
| 26 | Methyl | H | 1 | 4-Sulfoanilino |
| 27 | Methyl | H | 1 | Phenoxy |
| 28 | Methyl | H | 1 | 2-Aminoethylamino |
| 29 | H | Methoxy | 1 | Butylamino |
| 30 | H | Methoxy | 1 | Carboxymethylamino |
| 31 | H | Methoxy | 1 | 2-Carboxyphenylthio |
| 32 | H | Methoxy | 1 | 2-Carboxyethylthio |
| 33 | H | H | 1 | Butylamino |
| 34 | H | H | 1 | Carboxymethylamino |
| 35 | H | H | 1 | 2-Carboxyphenylthio |
| 36 | H | H | 1 | 2-Carboxyethylthio |
| 37 | Methyl | Methoxy | 1 | Butylamino |
| 38 | Methyl | Methoxy | 1 | Carboxymethylamino |
| 39 | Methyl | Methoxy | 1 | 2-Carboxyphenylthio |
| 40 | Methyl | Methoxy | 1 | 2-Carboxyethylthio |
| 41 | Methyl | H | 1 | Chloro |
| 42 | Methyl | H | 2 | Chloro |

The anthrapyridone compound of the present invention is produced by, for example, the following method. In this regard, in the following formulas (6) to (10) and the formula (A), $R_1$, $R_2$, $R_3$, n and X have the same meanings as those described above.

The anthrapyridone compound represented by the above formula (1) is obtained in, for example, the following manner.

That is, 1 mol of an anthraquinone compound represented by the following formula (6) and 1.1 to 3 mol of ethyl benzoylacetate substituted by $R_2$ are reacted in a polar solvent such as xylene in the presence of a basic compound such as sodium carbonate at 130 to 180° C. for 5 to 15 hours, to obtain a compound represented by the following formula (7).

Formula (6)

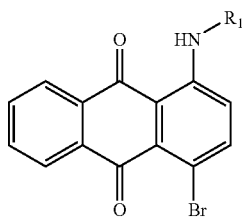

(6)

Formula (7)

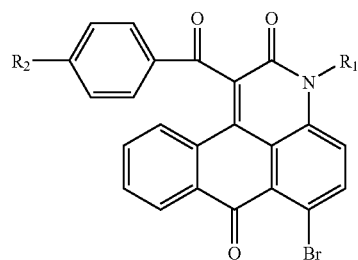

(7)

One mol of the obtained compound of the above formula (7) and 1 to 5 mol of meta-aminoacetoanilide are condensed by Ullmann reaction in an aprotic polar organic solvent such as N,N-dimethylformamide in the presence of a base such as sodium carbonate and a copper catalyst such as copper acetate at 110 to 150° C. for 2 to 6 hours, to obtain a compound of the following formula (8).

Formula (8)

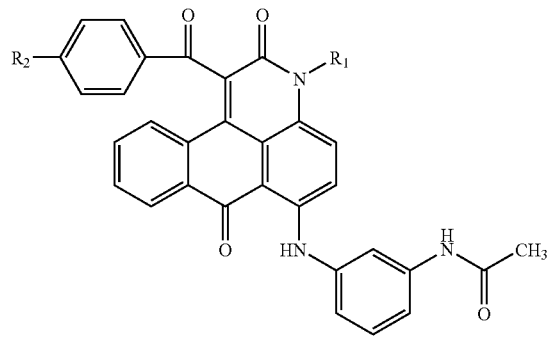

(8)

The obtained compound of the above formula (8) is sulfonated in 8 to 15% fuming sulfuric acid at 50 to 120° C. and at the same time, the acetylamino group is hydrolyzed, to obtain a compound represented by the following formula (9).

Formula (9)

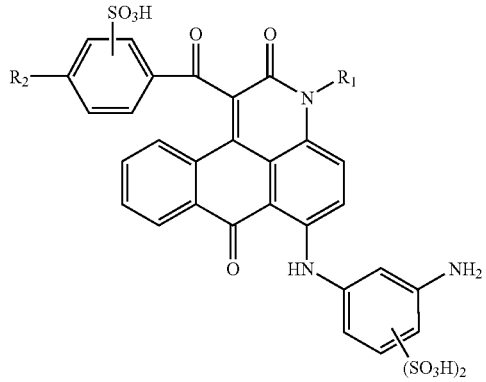

(9)

One mol of the obtained compound of the above formula (9) and 2 to 2.5 mol of a compound represented by, for example, the following formula (A) are reacted in water at pH 2 to 9 and 2 to 15° C. for 30 minutes to 1 hour. The obtained compound of the following formula (10) is reacted with 2 to 5 mol of a compound corresponding to $R_3$, i.e. a compound represented by "$R_3$—H" or the like at pH 7 to 10 and 20 to 90° C. for 10 minutes to 10 hours so that a leaving group X is substituted by $R_3$ in the formula (10), and thus a compound represented by the above formula (1) can be obtained.

Formula (A)

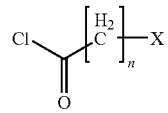

(A)

Formula (10)

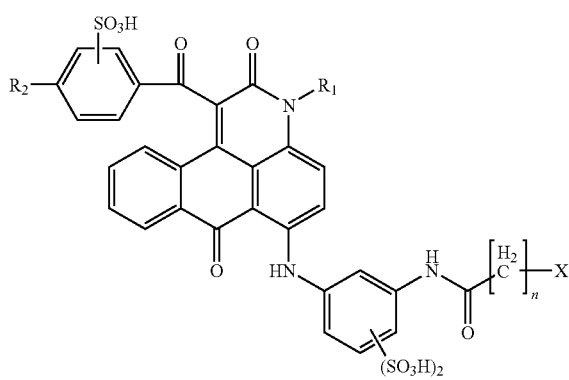

(10)

The compounds of the present invention is suitable as a magenta coloring matter for dyeing natural and synthetic textiles or textile blend, and further these compounds are suitable for production of inks for writing and ink compositions for inkjet recording.

When the compound represented by the above formula (1) is used as a coloring matter contained in an ink composition, it is preferred to use the compound containing a less content of inorganic substances (which are referred to as "inorganic impurities" in the present description) such as metal cation chloride and sulfate which are contained as impurities in said compound. The content of inorganic impurities is about, for example, 1% by mass or less relative to the total mass of the anthrapyridone compound of the present invention, only as a guide. In order to produce the compound of the present invention containing less inorganic impurities, the compound of the present invention obtained above may be subjected to desalting treatment by an ordinary method such as a method using, for example, a reverse osmosis membrane.

The ink composition of the present invention is a composition where the compound represented by the formula (1) is dissolved in water or an aqueous solvent (water containing a water-soluble organic solvent described later), according to necessity, together with an ink preparation agent, and a reaction liquid containing the compound represented by the formula (1) of the present invention can be directly used for production of an ink composition. It is also possible that an intended product is separated from the reaction liquid and dried, for example, spray-dried to obtain a dried form, which is then used for production of said ink composition. The ink composition for recording of the present invention contains the compound of the present invention in an amount of usually 0.1 to 20% by mass, more preferably 1 to 15% by mass and further preferably 2 to 10% by mass. The ink composition of the present invention may contain 0 to 30% by mass of a water-soluble organic solvent, 0 to 105% by mass and preferably 1 to 7% by mass of an ink preparation agent, respectively. The rest is water.

Specific examples of the above water-soluble organic solvent include, for example, C1 to C4 alkanol such as methanol, ethanol, n-propanol, isopropanol, n-butanol, isobutanol, secondary butanol and tertiary butanol; carboxylic acid amide such as N,N-dimethylformamide and N,N-dimethylacetoamide; lactam such as 2-pyrrolidone and N-methyl-2-pyrrolidone; cyclic urea such as 1,3-dimethylimidazolidin-2-one and 1,3-dimethylhexahydropyrimid-2-one; ketone or keto alcohol such as acetone, methyl ethyl ketone and 2-methyl-2-hydroxypentan-4-one; cyclic ether such as tetrahydrofuran and dioxane; mono-, oligo- or polyalkylene glycol or thioglycol having a C2 to C6 alkylene unit, such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, thiodiglycol, polyethylene glycol and polypropylene glycol; polyol (preferably triol) such as glycerine and hexane-1,2,6-triol; C1 to C4 alkyl ether of polyhydric alcohol such as ethylene glycol monomethyl ether, ethylene glycol monoethyl ether, diethylene glycol monomethyl ether, diethylene glycol monoethyl ether, butyl carbitol (diethylene glycol monobutyl ether), triethylene glycol monomethyl ether and triethylene glycol monoethyl ether; gamma-butyrolactone; dimethylsulfoxide; or the like. These water-soluble organic solvents are used alone or as a mixture thereof. It is preferred to appropriately use in combination of usually about 2 to 5 kinds.

Among them, preferable are 2-pyrrolidone, N-methyl-2-pyrrolidone, C1 to C4 alkanol, glycerine, mono-, di- or triethylene glycol, butyl carbitol and/or dipropylene glycol, and more preferably 2-pyrrolidone, N-methyl 2-pyrrolidone, isopropanol, glycerine and/or butyl carbitol.

Hereinafter, the ink preparation agents which can be used in preparation of the ink composition of the invention will be explained. Specific examples of the ink preparation agents include, for example, an antiseptic and fungicide, a pH adjuster, a chelating agent, a rust preventive agent, a water-soluble UV absorbing agent, a water-soluble polymer compound, a dye dissolving agent, a surfactant and the like.

The antiseptic and fungicide include, for example, compounds of organic sulfur-based, organic nitrogen sulfur-based, organic halogen-based, haloallylsulfone-based, iodopropargyl-based, N-haloalkylthio-based, benzothiazole-based, nitrile-based, pyridine-based, 8-oxyquinoline-based, isothiazoline-based, dithiol-based, pyridineoxide-based, nitropropane-based, organic tin-based, phenol-based, quaternary ammonium salt-based, triazine-based, thiadiazine-based, anilide-based, adamantane-based, dithiocarbamate-based, brominated indanone-based, benzyl bromoacetate-based, inorganic salt-based and the like.

The organic halogen-based compound includes, for example, sodium pentachlorophenol. The pyridineoxide-based compound includes, for example, sodium 2-pyridinethiol-1-oxide. The isothiazoline-based compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like. The other antiseptic and fungicide includes anhydrous sodium acetate, sodium sorbate, sodium benzoate and the like.

As the pH adjuster, any substance can be used as long as it can adjust the pH of the ink in the range of 8.0 to 11.0 without giving adverse effects on the ink to be mixed. It can include, for example, alkanolamine such as diethanolamine and triethanolamine; alkali metal hydroxide such as lithium hydroxide, sodium hydroxide and potassium hydroxide; ammonium hydroxide; alkali metal carbonate such as lithium carbonate, sodium carbonate and potassium carbonate; and the like.

The chelating agent includes, for example, sodium ethylenediaminetetraacetate, sodium nitrilotriacetate, sodium hydroxyethylethylenediaminetriacetate, sodium diethylenetriaminepentaacetate, sodium uracildiacetate and the like.

The rust preventive agent includes, for example, hydrogen sulfite salt, sodium thiosulfate, ammonium thioglycolate, diisopropylammonium nitrite, pentaerythritol tetranitrate, dicyclohexylammonium nitrite and the like.

The water-soluble UV absorbing agent includes, for example, sulfonated benzophenone, sulfonated benzotriazole or the like.

The water-soluble polymer compound includes, for example, polyvinyl alcohol, cellulose derivatives, polyamine, polyimines and the like.

The dye dissolving agent includes, for example, urea, epsilon-caprolactam, ethylene carbonate and the like.

Examples of the surfactant include, for example, known surfactants such as anion-based, cation-based or nonion-based surfactants.

Examples of the anionic surfactant include alkyl sulfonate, alkyl carboxylate, alpha-olefin sulfonate, polyoxyethylene alkyl ether acetate, N-acylamino acid and a salt thereof, N-acylmethyltaurine salt, alkylsulfate polyoxyalkyl ether sulfate, alkylsulfate polyoxyethylene alkyl ether phosphate, rosin acid soap, castor oil sulfate, lauryl alcohol sulfate, alkylphenol type phosphate ester, alkyl type phosphate ester, alkylallylsulfonate, diethylsulfosuccinate, diethylhexylsulfosuccinate, dioctylsulfosuccinate and the like.

The cationic surfactant includes 2-vinylpyridine derivatives, poly(4-vinylpyridine) derivatives and the like.

Specific examples of the amphoteric surfactant include lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, and in addition, imidazoline derivatives and the like.

Specific examples of the nonionic surfactant includes ether-based surfactants such as polyoxyethylene nonylphenyl ether, polyoxyethylene octylphenyl ether, polyoxyethylene dodecylphenyl ether, polyoxyethylene oleyl ether, polyoxyethylene lauryl ether and polyoxyethylene alkyl ether; ester-based surfactants such as polyoxyethylene oleate ester, polyoxyethylene distearate ester, sorbitan laurate, sorbitan monostearate, sorbitan monooleate, sorbitan sesquioleate, polyoxyethylene monooleate and polyoxyethylene stearate; acetylene glycol (alcohol)-based surfactants such as 2,4,7,9-tetramethyl-5-decyne-4,7-diol, 3,6-dimethyl-4-octyne-3,6-diol and 3,5-dimethyl-1-hexyn-3 of (for example, trade name: Surfynol® 104, 105, 82, 465, Olfine® STG and the like manufactured by Nissin Chemical Industry Co., Ltd.); polyglycol ether-based surfactants (for example, Tergitol® 15-S-7 and the like manufactured by SIGMA-ALDRICH); and the like. These ink preparation agents are used alone or as a mixture thereof.

The water-based ink composition of the present invention can be produced by dissolving the compound of the present invention (compound represented by the formula (1) and/or a salt thereof, which is also referred to as the present compound, hereinafter) in water or the above aqueous solvent (water containing a water-soluble organic solvent), according to necessity, together with the above ink preparation agents and the like.

In the above production method, the order to dissolve the components is not particularly limited. The present compound may be dissolved in water or the above aqueous solvent in advance and an ink preparation agent may be added and dissolved, or the present compound may be dissolved in water and then an aqueous solvent and an ink preparation agent may be added and dissolved. In addition, the order may be different from this, and therefore an aqueous solvent and an ink preparation agent may added to a reaction liquid of the present compound or to the liquid subjected to desalting treatment using a reverse osmosis membrane for production of the ink composition.

In preparation of the ink composition, water used is preferably water containing less impurity, such as ion-exchanged water or distilled water. In addition, microfiltration may be carried out, according to necessity, using a membrane filter for removing foreign substances. Further, when the ink composition is used as an ink for inkjet printer, it is preferred to carry out microfiltration. The pore size of filter for microfiltration is usually 1 to 0.1 µm and preferably 0.8 to 0.2 µm.

The magenta ink composition containing the water-soluble anthrapyridone compound of the present invention is suitable for use in impress printing, copying, marking, writing, drafting, stamping or recording, particularly in inkjet recording. In this case, high quality printed matter of magenta having good durability against water, sunlight, ozone and friction can be obtained. In addition, it is also possible to change the color tone before mixing to a preferable orange or red color tone by mixing the compound of the present invention with a known and widely-used dye of yellow, magenta or the like. Further, it can be also used for color toning to express another color, particularly black.

The colored product of the present invention is a product colored with the above compound of the present invention. Materials to be colored are not particularly limited and include, for example, paper, fiber and cloth (cellulose, nylon, wool and the like), leather, substrates for color filters, and the like, but not limited thereto. The method of coloration includes, for example, printing methods such as dip dyeing, textile printing and screen printing, a method by inkjet recording, and the like, and a method by inkjet recording is preferable in the present invention.

The record-receiving material (media) which can be recorded by the inkjet recording method of the present invention include, for example, communication sheet such as paper and film, fiber, leather, and the like. The communication sheet is preferably subjected to surface treatment, and specifically communication sheet where an ink receiving layer is provided on such a substrate is preferable. The ink receiving layer is provided by, for example, impregnating or coating the above substrate with a cation polymer; by coating the above substrate surface with a porous white inorganic substance capable of absorbing coloring matter in ink, such as porous silica, aluminasol and special ceramics, together with a hydrophilic polymer such as polyvinyl alcohol and polyvinylpyrrolidone. Such communication sheet provided with an ink receiving layer is called usually inkjet special paper (film) or glossy paper (film) and includes, for example, Pictorico® (which is manufactured by Asahi Glass Co., Ltd.), Professional Photopaper, Super Photopaper and Matte Photopaper, (which are all manufactured by Canon Inc.), Photo Paper <glossy>, Photo Matte Paper and Super Fine Glossy Film (which are all manufactured by Seiko-Epson Corporation), Premium Plus Photo Paper, Premium Glossy Film and Photo Paper (which are all manufactured by Hewlett-Packard Japan, Ltd.), PhotoLikeQP (which is manufactured by KONICA Corporation) and the like. In this regard, plain paper can be naturally used.

It is known among them that when a record-receiving material whose surface is coated with a porous white inorganic substance is used, discoloration or fading of recorded images caused by ozone gas is particularly developed. However, the water-based magenta ink composition of the present invention is superior in ozone gas fastness and therefore exerts a superior effect on storage stability of images recorded on such a record-receiving material.

The porous white inorganic substance to be used for such a purpose includes calcium carbonate, kaolin, talc, clay, diatom earth, synthesized amorphous silica, aluminum silicate, magnesium silicate, calcium silicate, aluminum hydroxide, alumina, lithopone, zeolite, barium sulfate, sulfuric acid calcium, titanium dioxide, zinc sulfide, zinc carbonate and the like.

In order to record on a record-receiving material by the inkjet recording method of the present invention, for example, a container containing the above ink composition is placed in its predetermined position of an inkjet printer and recording may be performed on a record-receiving material by an ordinary method. In inkjet recording method of the present invention, the magenta ink composition of the present invention can be used in combination with a green ink composition, an orange ink composition and a blue (or violet) ink composition and, according to necessity, a black ink composition and the like, in addition to a yellow ink composition and a cyan ink composition which are known and widely used. Each color ink composition is filled in each container, and these containers are placed (loaded) in their predetermined positions of an inkjet printer as well as a container containing a water-based magenta ink composition for inkjet recording of the present invention for use. The inkjet printer includes, for example, printers using piezo method with mechanical vibration; printers using Bubble Jet® method with bubbles generated by heating; and the like.

The water-based magenta ink composition of the present invention exhibits vivid magenta color, has a high vivid hue particularly on inkjet glossy paper, and allows high fastness of recorded images. In addition, it is highly safe for humans.

The ink composition of the present invention is free from precipitation and separation during storage. In addition, when the ink composition of the present invention is used for inkjet recording, it does not even cause clogging of the injector (inkhead). The ink composition of the present invention is free from changes in physical properties even under constant recirculation for relatively long hours by a continuous ink jet printer; under intermittent use by an on-demand printer; and the like.

EXAMPLES

Hereinafter, the present invention will be explained more specifically. In this regard, "part(s)" and "%" in the text are respectively based on mass unless otherwise specifically noted. In addition, the processes of reaction, crystallization and the like are all carried out under stirring unless otherwise specifically noted.

The solubility (at room temperature) to water of the present compound obtained in Examples is 100 g/L or more.

In addition, the maximum absorption wavelength (λmax) of the compounds in Examples is a value measured in an aqueous solution unless otherwise specifically noted.

Example 1

(1) To 360 parts of xylene, 94.8 parts of a compound of the following formula (11), 3.0 parts of sodium carbonate and 144.0 parts of ethyl benzoylacetate were sequentially added, the temperature was raised, and the reaction was carried out at a temperature of 140 to 150° C. for 8 hours. Meanwhile, ethanol and water generated in the reaction was distilled off out of the system as a xylene azeotrope, and the reaction was completed. Then, the reaction liquid was cooled, 240 parts of methanol was added at 30° C., and after stirring for 30 minutes, the precipitated solid was separated by filtration. The resulting solid was washed with 360 parts of methanol and then dried to obtain 124.8 parts of a compound represented by the following formula (12) as pale yellow needle crystals.

Formula (11)

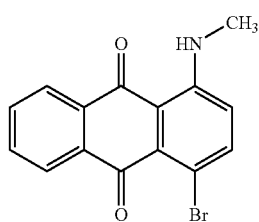

(11)

Formula (12)

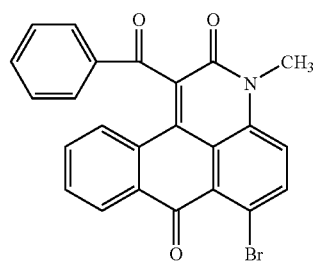

(12)

(2) To 300.0 parts of N,N-dimethylformamide, 88.8 parts of the compound of the above formula (12), 75.0 parts of meta-aminoacetoanilide, 24.0 parts of copper acetate monohydrate and 12.8 parts of sodium carbonate were sequentially added, the temperature was raised to 120 to 130° C., and the reaction was carried out for 3 hours. The reaction liquid was cooled to about 50° C., 120 parts of methanol was added thereto, and the mixture was stirred for 30 minutes. The precipitated solid was separated by filtration, washed with 500 parts of metha-nol and then with hot water of 80° C., followed by drying to obtain 79.2 parts of a compound of the following formula (13) as bluish red crystals.

Formula (13)

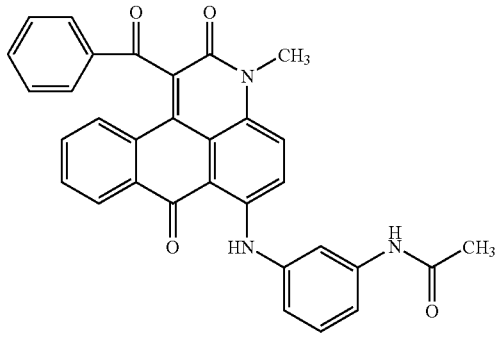

(13)

(3) To 130 parts of 98% sulfuric acid, 170 parts of 28% fuming sulfuric acid was added while water-cooling to prepare 300 parts of 12% fuming sulfuric acid. After 51.3 parts of the compound represented by the above formula (13) was added thereto at 50° C. or less under water-cooling, the temperature was raised to 85 to 90° C., and the reaction was carried out for 4 hours. To 600 parts of ice water, the reaction liquid was added, while adding ice to maintain the liquid temperature at 40° C. or less in view of exothermic heat. In addition, water was added thereto to make the liquid volume 1000 parts, followed by filtration to remove insoluble substances off. Hot water was added to the resulting mother liquid to make the volume 1500 parts, 300 parts of sodium chloride was added thereto and the mixture was stirred for 2 hours while maintaining the liquid temperature at 60 to 65° C., and the precipitated crystals were separated by filtration. The resulting crystals was washed with 300 parts of a 20% aqueous sodium chloride solution, and water was well squeezed to obtain 100.3 parts of a wet cake containing 59.2 parts of a compound of the following formula (14) as red crystals.

Formula (14)

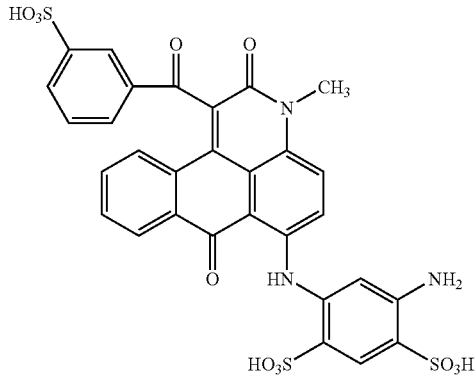

(14)

(4) To 1000 parts of water, 1300 parts of the wet cake of the formula (14) obtained in the above Example 1 (3) and 500 parts of 25% sodium hydroxide were added, and completely dissolved. The concentration of this compound in solution determined by diazo analysis method was 24.35%. To 20 parts of water, 64 parts of this solution was added and the liquid temperature was adjusted to 10° C. or less while ice-cooling. Hereto, 5.8 parts of chloroacetyl chloride was added, and the mixture was stirred for 30 minutes at 10° C. while maintaining at pH 2.5. The adjustment of the pH was carried out with a 25% aqueous sodium hydroxide solution. This reaction liquid was adjusted to 50 to 60° C., 20 parts of sodium chloride was added thereto and the mixture was stirred, and the precipitated crystals was separated by filtration. The resulting crystals was washed with 100 parts of a 22% aqueous sodium chloride solution, and water was well squeezed to 34 parts of a wet cake of sodium salt of a compound of the following formula (15) (Compound No. 41 in Table 1). The λmax (maximum absorption wavelength) of the obtained compound was 534 nm.

adjusted to pH 0.5 with 35% hydrochloric acid at a liquid temperature of 50 to 55° C., 30 parts of ammonium chloride was added thereto, the mixture was stirred, and the precipitated solid was separated by filtration. The resulting solid was washed with 100 parts of a 23% aqueous ammonium chloride solution, the resulting wet cake was added to 100 parts of methanol, the mixture was heated with stirring, and the resulting solid was washed with methanol and dried to obtain 16 parts of ammonium salt of a compound of the following formula (16) (compound No. 2 in Table 1) as a red solid. The λmax (maximum absorption wavelength) was 531 nm.

Formula (16)

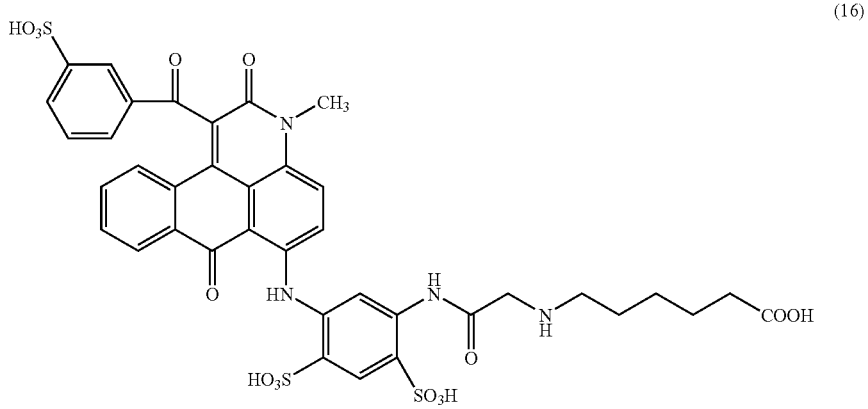

(16)

Formula (15)

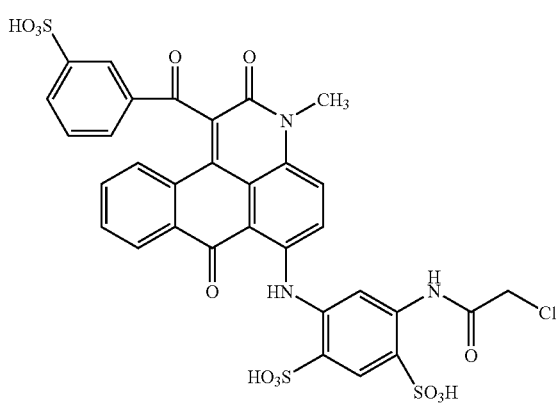

(15)

Example 2

To a wet cake containing 17 parts of the compound of the formula (15) obtained in the above Example 1 (4), water was added to make the total amount 89 parts, and the wet cake was dissolved. The temperature of the solution was raised to 60° C., the pH was adjusted to pH 10, 13 parts of 6-aminohexanoic acid was added thereto, and the mixture was stirred for 30 minutes. The adjustment of the pH was carried out with a 25% aqueous sodium hydroxide solution. The liquid was

Example 3

To a wet cake containing 17 parts of the compound of the formula (15) obtained in the above Example 1 (4), water was added to make the total amount 89 parts and the wet cake was dissolved. The temperature of the liquid was raised to 60° C., the pH was adjusted to pH 10, 13 parts of 6-aminohexanoic acid was added thereto, and the mixture was stirred for 30 minutes. The adjustment of pH was carried out with a 25% aqueous sodium hydroxide solution. The liquid was adjusted to pH 0.5 with 35% hydrochloric acid at a liquid temperature of 50 to 55° C., and 30 parts of sodium chloride was added thereto, the mixture was stirred, and the precipitated solid was separated by filtration. This was washed with 100 parts of a 22% aqueous sodium chloride solution, the resulting wet cake was added to 100 parts of methanol, the mixture was heated with stirring, and the resulting solid was filtered, washed with methanol and dried to obtain 9 parts of sodium salt of a compound of the above formula (16) (compound No. 2 in Table 1) as a red solid.

Example 4

To a wet cake containing 10.7 parts of the compound of the formula (15) obtained in the above Example 1 (4), 100 parts of water was added, the wet cake was dissolved. The temperature of the solution was raised to 60° C., the pH was adjusted to pH 8, 4.6 parts of butylamine added thereto, and the mixture was stirred for 1 hour 30 minutes. The adjustment of pH was carried out with a 25% aqueous sodium hydroxide solution. The pH was adjusted to pH 1.8 with 35% hydrochloric acid at a liquid temperature of 50 to 55° C., 24 parts of ammonium chloride was added thereto, the mixture was stirred, and the precipitated solid was separated by filtration.

This was washed with 100 parts of a 23% aqueous ammonium chloride solution, the resulting wet cake was added to 100 parts of methanol, the mixture was heated with stirring, and the resulting solid was filtered, washed with methanol and dried to obtain 4.0 parts of ammonium salt of a compound of the following formula (17) (No. 1' in Table 1) as a red solid. The λmax (maximum absorption wavelength) was 531 nm.

Formula (17)

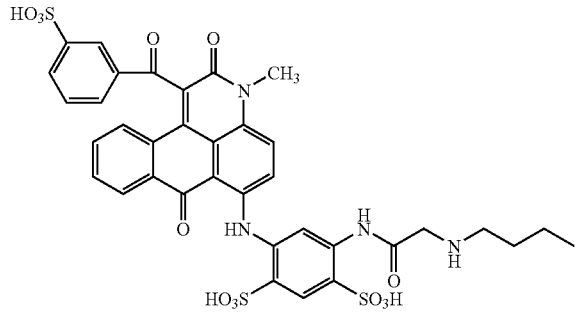

(17)

Example 5

To a wet cake containing 8.5 parts of the compound of the formula (15) obtained in the above Example 1 (4), 100 parts of water was added, and the wet cake was dissolved. The solution was adjusted to 35° C. and pH 8 while stirring, 1.7 parts of thiosalicylic acid was added thereto, and the mixture was stirred for 3 hours. The adjustment of pH was carried out with a 25% aqueous sodium hydroxide solution. The liquid was adjusted to pH 4.0 with 35% hydrochloric acid at a liquid temperature of 50 to 55° C. Thereto, 43.2 parts of ammonium chloride was added, the mixture was stirred, and the precipitated solid was separated by filtration. This was washed with 100 parts of a 23% aqueous ammonium chloride solution, the resulting wet cake was added to 100 parts of methanol, the mixture was heated with stirring, and the resulting solid was washed with methanol and dried to obtain 7.8 parts of ammonium salt of a compound of the following formula (18) (compound No. 4 in Table 1) as a red solid. The λmax (maximum absorption wavelength) was 530 nm.

Formula (18)

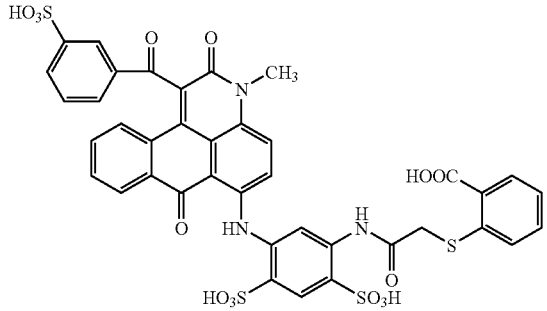

(18)

Example 6

To a wet cake containing 8.5 parts of the compound of the formula (15) obtained in the above Example 1 (4), 100 parts of water was added, and the wet cake was dissolved. The temperature of the solution was raised to 60° C., the pH was adjusted to pH 8, 2.0 parts of 3-mercaptopropionic acid was added thereto and the mixture was stirred for 10 hours. The adjustment of pH was carried out with a 25% aqueous sodium hydroxide solution. The liquid was adjusted to pH 1.2 with 35% hydrochloric acid at a liquid temperature of 50 to 55° C., 26 parts of ammonium chloride was added thereto, the mixture was stirred, and the precipitated solid was separated by filtration. This was washed with 100 parts of a 23% aqueous ammonium chloride solution, the resulting wet cake was added to 100 parts of methanol, the mixture was heated with stirring, and the resulting solid was filtered, washed with methanol and dried to obtain 5.0 parts of ammonium salt of a compound of the following formula (19) (No. 3 in Table 1) as a red solid. The λmax (maximum absorption wavelength) was 532 nm.

Formula (19)

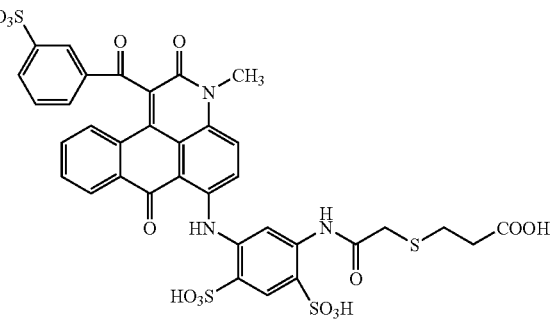

(19)

Example 7

To a wet cake containing 8.5 parts of the compound of the formula (15) obtained in the above Example 1 (4), 100 parts of water was added, and the wet cake was dissolved. The temperature of the solution was raised to 60° C., the pH was adjusted to pH 8, 5.4 parts of benzylamine was added, and the mixture was stirred for 3 hours. The adjustment of pH was carried out with a 25% aqueous sodium hydroxide solution. The liquid was adjusted to pH 1.1 with 35% hydrochloric acid at a liquid temperature of 50 to 55° C., 22.5 parts of ammonium chloride was added thereto, the mixture was stirred, and the precipitated solid was separated by filtration. This was washed with 100 parts of an 18% aqueous ammonium chloride solution, the resulting wet cake was added to 100 parts of methanol, the mixture was heated with stirring, and the resulting solid was filtered, washed with methanol and dried to obtain 8.5 parts of ammonium salt of a compound of the following formula (20) (compound No. 5 in Table 1) as a red solid. The λmax (maximum absorption wavelength) was 531 nm.

Formula (20)

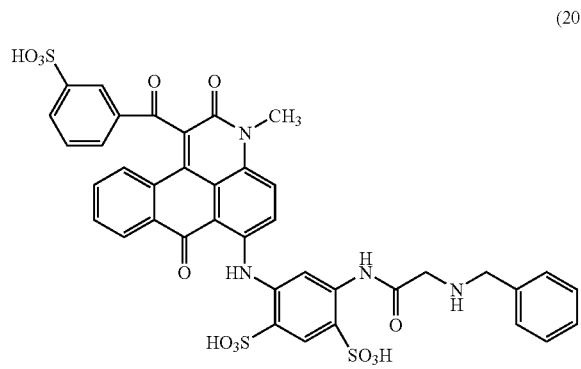

Formula (21)

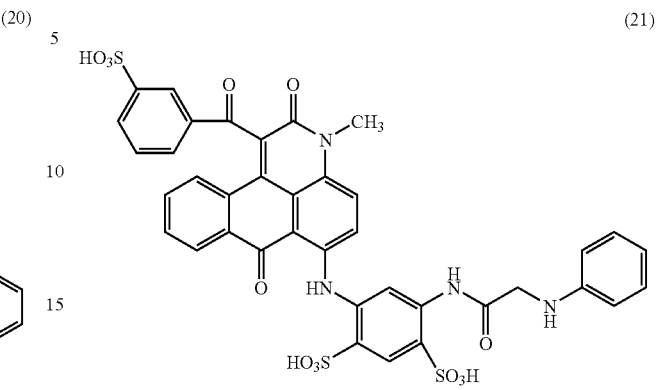

Example 8

To a wet cake containing 8.5 parts of the compound of the formula (15) obtained in the above Example 1 (4), 100 parts of water was added, and the wet cake was dissolved. The temperature of the solution was raised to 60° C., and the pH was adjusted to pH 8, 4.7 parts of aniline was added, and the mixture was stirred for 5 hours. The adjustment of pH was carried out with a 25% aqueous sodium hydroxide solution. The liquid was adjusted to pH 1.7 with 35% hydrochloric acid at a liquid temperature of 50 to 55° C., 12 parts of ammonium chloride was added thereto, the mixture was stirred, and the precipitated solid was separated by filtration. This was washed with 100 parts of a 10% aqueous ammonium chloride solution, the resulting wet cake was added to 100 parts of methanol, the mixture was heated with stirring, and the resulting solid was filtered, washed with methanol and dried to obtain 5.5 parts of ammonium salt of a compound of the following formula (21) (compound No. 6 in Table 1) as a red solid. The λmax (maximum absorption wavelength) was 532 nm.

Example 9

To a wet cake containing 4.3 parts of the compound of the formula (15) obtained in the above Example 1 (4), 100 parts of water was added, and the wet cake was dissolved. The temperature of the liquid was raised to 40° C., the pH was adjusted to pH 8, 1.5 parts of octanethiol was added thereto, and the mixture was stirred for 3 hours. The adjustment of pH was carried out with a 25% aqueous sodium hydroxide solution. Acetone was added to the reaction liquid, the precipitated solid was dissolved in water and adjusted to pH 0.7 with 35% hydrochloric acid at 50 to 55° C., and 27.8 parts of ammonium chloride was added. To an oily precipitate obtained by removing the aqueous solution off by decantation, ethanol was added for solidification, and then the resulting solid was removed by filtration and dried to obtain 1.3 parts of ammonium salt of a compound of the following formula (22) (compound No. 7 in Table 1) as a red solid. The λmax (maximum absorption wavelength) was 534 nm.

Formula (22)

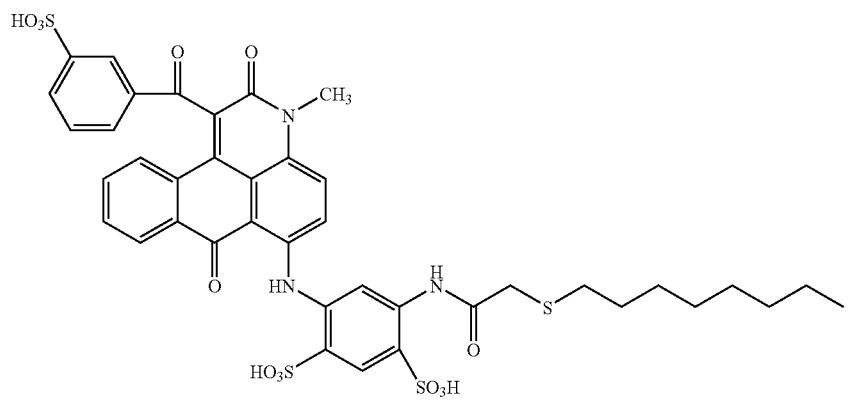

Example 10

To a wet cake containing 8.5 parts of the compound of the formula (15) obtained in the above Example 1 (4), 100 parts of water was added, and the wet cake was dissolved. The temperature of the solution was raised to 60° C., the liquid was adjusted to pH 8, 5.1 parts of hexylamine was added thereto, and the mixture was stirred for 3 hours. The adjustment of pH was carried out with a 25% aqueous sodium hydroxide solution. The liquid was adjusted to pH 1.0 with 35% hydrochloric acid at a liquid temperature of 50 to 55° C., 30 parts of ammonium chloride was added thereto, the mixture was stirred and the precipitated solid was separated by filtration. This was washed with 100 parts of an 18% aqueous ammonium chloride solution, the resulting wet cake was dissolved in a small amount of methanol, and isopropylalcohol was added to precipitate a solid. The precipitated solid was filtered and dried to obtain 5.2 parts of ammonium salt of a compound of the following formula (23) (compound No. 8 in Table 1) as a red solid. The λmax (maximum absorption wavelength) was 529 nm.

Formula (23)

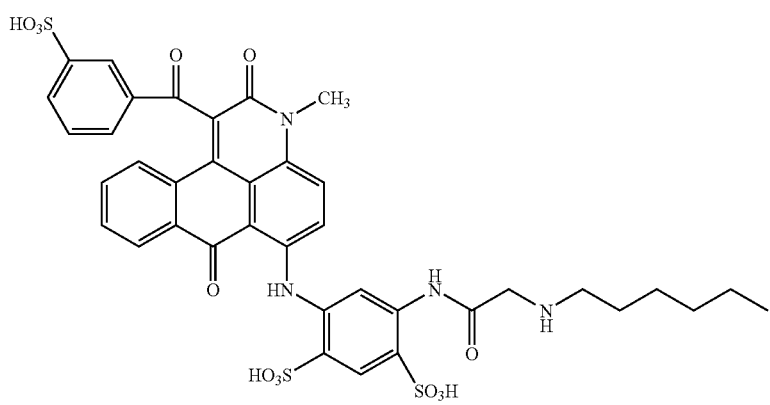

(23)

Formula (24)

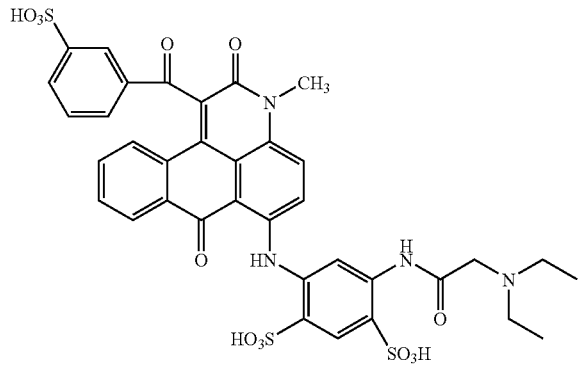

(24)

Example 11

To a wet cake containing 8.5 parts of the compound of the formula (15) obtained in the above Example 1 (4), 100 parts of water was added, and the wet cake was dissolved. The temperature of the solution was raised to 60° C., the pH was adjusted to pH 7.5, 2.5 parts of diethylamine was added thereto, and the mixture was stirred for 3 hours. The adjustment of pH was carried out with a 25% aqueous sodium hydroxide solution. The liquid was adjusted to pH 2.0 with 35% hydrochloric acid at a liquid temperature of 50 to 55° C., 20 parts of ammonium chloride was added thereto, the mixture was stirred, and the precipitated solid was separated by filtration. This was washed with 100 parts of a 23% aqueous ammonium chloride solution, the resulting wet cake was added to 100 parts of methanol, the mixture was heated with stirring, and the resulting solid was filtered, washed with methanol and dried to obtain 4.1 parts of ammonium salt of a compound of the following formula (24) (compound No. 10 in Table 1) as a red solid. The λmax (maximum absorption wavelength) was 530 nm.

Example 12

To a wet cake containing 8.5 parts of the compound of the formula (15) obtained in the above Example 1 (4), 100 parts of water was added, and the wet cake was dissolved. The temperature of the solution was raised to 60° C., the pH was adjusted to pH 7.5, 10.2 parts of diisopropylamine was added thereto, and the mixture was stirred for 4.5 hours. The adjustment of pH was carried out with a 25% aqueous sodium hydroxide solution. The liquid was adjusted to pH 1.7 with 35% hydrochloric acid at a liquid temperature of 50 to 55° C., 20 parts of ammonium chloride was added thereto, the mixture was stirred, and the precipitated solid was separated by filtration. This was washed with 100 parts of a 23% aqueous ammonium chloride solution, the resulting wet cake was added to 100 parts of methanol, the mixture was heated with stirring, and the resulting solid was filtered, washed with methanol and dried to obtain 2.2 parts of ammonium salt of a compound of the following formula (25) (compound No. 11 in Table 1) as a red solid. The λmax (maximum absorption wavelength) was 531 nm.

Formula (25)

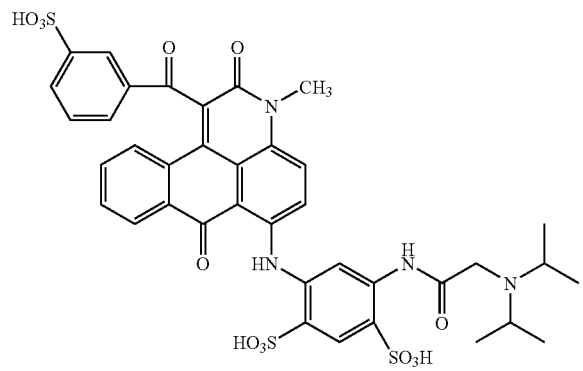

(25)

Example 13

To a wet cake containing 8.5 parts of the compound of the formula (15) obtained in the above Example 1 (4), 100 parts of water was added, and the wet cake was dissolved. The temperature of the solution was raised to 60° C., the pH was adjusted to pH 7.5, 4.1 parts of anthranilic acid was added thereto, and the mixture was stirred for 10 hours. The adjustment of pH was carried out with a 25% aqueous sodium hydroxide solution. The liquid was adjusted to pH 3.8 with 35% hydrochloric acid at a liquid temperature of 50 to 55° C., 16.5 parts of ammonium chloride was added thereto, the mixture was stirred, and precipitated solid was separated by filtration. This was washed with 100 parts of an 18% aqueous ammonium chloride solution, the resulting wet cake was added to 100 parts of methanol, the mixture was heated with stirring, and the resulting solid was filtered, washed with methanol and dried to obtain 7.7 parts of ammonium salt of a compound of the following formula (26) (compound No. 19 in Table 1) as a red solid. The λmax (maximum absorption wavelength) was 530 nm.

Formula (26)

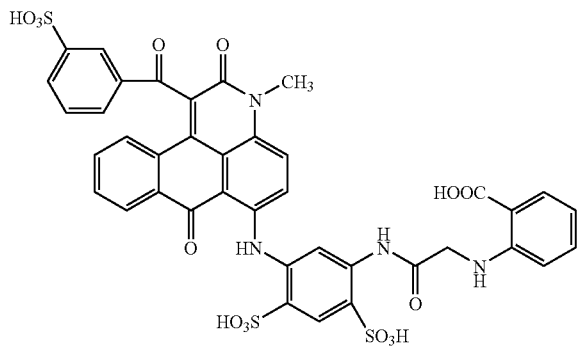

(26)

Example 14

To a wet cake containing 17 parts of the compound of the formula (15) obtained in the above Example 1 (4), 100 parts of water was added, and the wet cake was dissolved. The temperature of the solution was raised to 70° C., the pH was adjusted to pH 9.0, 12.0 parts of taurine was added thereto, and the mixture was stirred for 1 hour. The adjustment of pH was carried out with a 25% aqueous sodium hydroxide solution. Thereto, 400 parts of ethanol was added at a liquid temperature of 50 to 55° C. To an oily precipitate obtained by removing the supernatant liquid off by decantation, 100 parts of water was added to make it a solution, the solution was adjusted to pH 6.5 with 3.5% hydrochloric acid at 50° C., 200 parts of methanol was then added dropwise followed by cooling, and then the precipitated solid was separated by filtration and dried to obtain 13.0 parts of sodium salt of a compound of the following formula (27) (compound No. 24 in Table 1) as a red solid.

Formula (27)

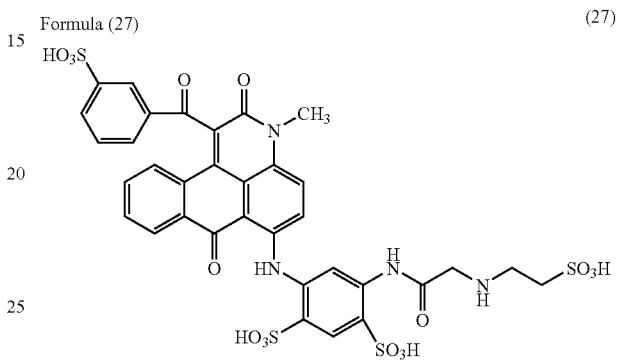

(27)

Example 15

To a wet cake containing 8.5 parts of the compound of the formula (15) obtained in the above Example 1 (4), 50 parts of water was added, and the wet cake was dissolved. The temperature of the solution was raised to 60° C., the pH was adjusted to pH 9.0, 3.8 parts of glycine was added thereto, and the mixture was stirred for 4 hours. The adjustment of pH was carried out with a 25% aqueous sodium hydroxide solution. The liquid was adjusted to pH 1.0 with 35% hydrochloric acid at a liquid temperature of 40° C., and 150 parts of ethanol was added thereto. To an oily precipitate obtained by removing the supernatant liquid by decantation, 50 parts of water was added to make it a solution, 100 parts of ethanol was added thereto at room temperature, and the precipitated solid was removed by filtration and dried to obtain 4.6 parts of a compound of the following formula (28) (compound No. 22 in Table 1) as a red solid. In this regard, this compound is a compound which is partially sodium salt.

Formula (28)

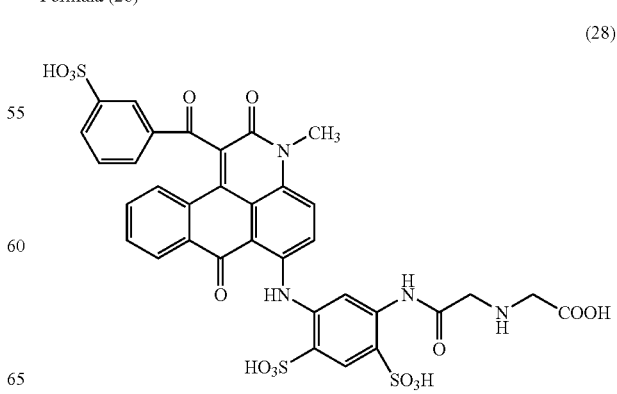

(28)

Example 16

In the same manner as that of the above Example 1 (4), 108 parts of a solution containing a compound of the above formula (14) having a concentration of 24.35%, by diazo analysis method was obtained. To this solution, 40 parts of acetone was added, and the mixture was cooled to 10° C. or less while stirring under ice-cooling. Hereto, 8.1 parts of chloropropionyl chloride was added, the liquid was stirred for 3 hours while maintaining at pH 2.5 with a 25% aqueous sodium hydroxide solution at a liquid temperature of 10° C., and the precipitated solid was separated by filtration. Water was well squeezed to obtain 58 parts of a wet cake of sodium salt of a compound of the following formula (29) (compound No. 42 in Table 1).

Formula (29)

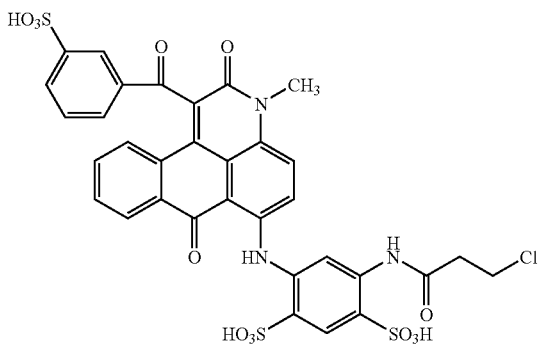

(29)

Example 17

To a wet cake containing 8.7 parts of the compound of the formula (29) obtained in the above Example 16, 100 parts of water was added, and the wet cake was dissolved. The temperature of the solution was raised to 60° C., the pH was adjusted to pH 7.5, 3.7 parts of butylamine was added thereto, and the mixture was stirred for 3 hours. The adjustment of pH was carried out with a 25% aqueous sodium hydroxide solution. The liquid was adjusted to pH 2.7 with 35% hydrochloric acid at a liquid temperature of 50 to 55° C., 7.5 parts of ammonium chloride was added thereto, the mixture was stirred, and precipitated solid was separated by filtration. This was washed with 100 parts of an 8% aqueous ammonium chloride solution, the resulting wet cake was added to 100 parts of methanol, and the mixture was heated with stirring, and the resulting solid was filtered, washed with methanol and dried to obtain 5.7 parts of ammonium salt of a compound of the following formula (30) (compound No. 13 in Table 1) as a red solid. The λmax (maximum absorption wavelength) was 533 nm.

Formula (30)

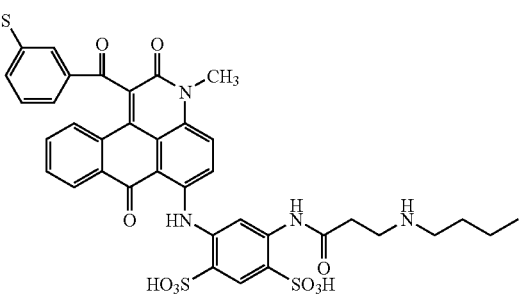

(30)

Example 18

To a wet cake containing 8.7 parts of the compound of the formula (29) obtained in the above Example 16, 100 parts of water was added, and the wet cake was dissolved. The temperature of the solution was raised to 60° C., the pH was adjusted to pH 7.5, 4.6 parts of thiosalicylic acid was added thereto, and the mixture was stirred for 4 hours. The adjustment of pH was carried out with a 25% aqueous sodium hydroxide solution. The liquid was adjusted at pH 4.4 with 35% hydrochloric acid at a liquid temperature of 50 to 55° C., 5.0 parts of ammonium chloride was added thereto, the mixture was stirred, and the precipitated solid was separated by filtration. This was washed with 100 parts of an 8% aqueous ammonium chloride solution, the resulting wet cake was added to 100 parts of methanol, the mixture was heated with stirring, and the resulting solid was filtered, washed with methanol and dried to obtain 7.3 parts of ammonium salt of a compound of the following formula (31) (compound No. 9 in Table 1) as a red solid. The λmax (maximum absorption wavelength) was 534 nm.

Formula (31)

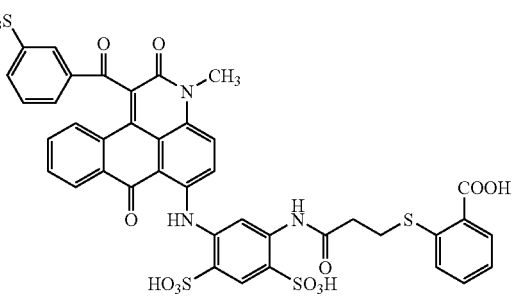

(31)

Example 19

To a wet cake containing 8.7 parts of the compound of the formula (29) obtained in the above Example 16, 100 parts of water was added, and the wet cake was dissolved. The temperature of the solution was raised to 60° C., the pH was adjusted to pH 7.5, 4.1 parts of 6-aminohexanoic acid and 0.2 parts of potassium iodide were added thereto, and the mixture was stirred for 10 hours. The adjustment of pH was carried out with a 25% aqueous sodium hydroxide solution. The liquid was adjusted to pH 1.2 with 35% hydrochloric acid at a liquid temperature of 50 to 55° C., 30 parts of ammonium chloride was added thereto, the mixture was stirred, and the precipitated solid was separated by filtration. The resulting wet cake was added to 100 parts of methanol, the mixture was heated with stirring, and the resulting solid was filtered, washed with methanol and dried to obtain 4.2 parts of ammonium salt of a compound of the following formula (32) (compound No. 12 in Table 1) as a red solid. The λmax (maximum absorption wavelength) was 530 nm.

Formula (32)

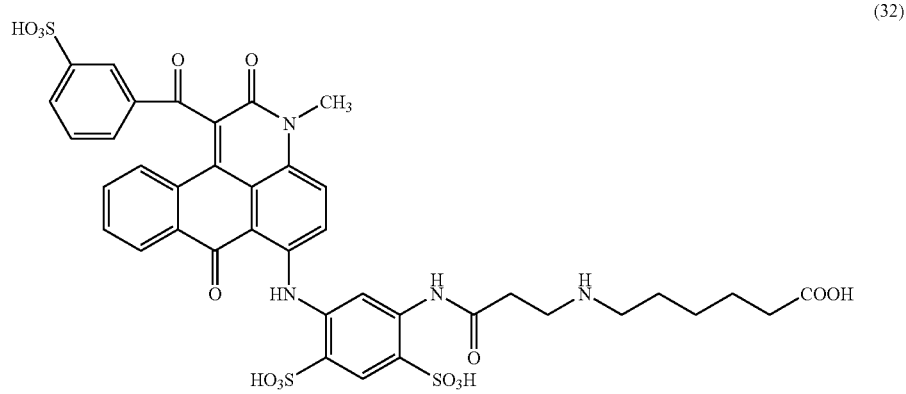

(32)

Example 20

To a wet cake containing 8.5 parts of the compound of the formula (15) obtained in the above Example 1 (4), 100 parts of water was added, and the wet cake was dissolved. The temperature of the solution was raised to 45° C., the pH was adjusted to pH 9.5, 72.0 parts of phenol was added thereto, and the mixture was stirred for 4 days. The adjustment of pH was carried out with a 25% aqueous sodium hydroxide solution. The liquid was adjusted to pH 2.0 with 35% hydrochloric acid at a liquid temperature of 50 to 55° C., 20 parts of sodium chloride was added thereto, the mixture was stirred, and the precipitated solid was separated by filtration. This was washed with 100 parts of a 22% aqueous sodium chloride solution, the resulting wet cake was added to 100 parts of methanol, the mixture was heated with stirring, and the resulting solid was filtered, washed with methanol and dried to obtain 2.9 parts of sodium salt of a compound of the following formula (33) (compound No. 27 in Table 1) as a red solid. The λmax (maximum absorption wavelength) was 531 nm.

Formula (33)

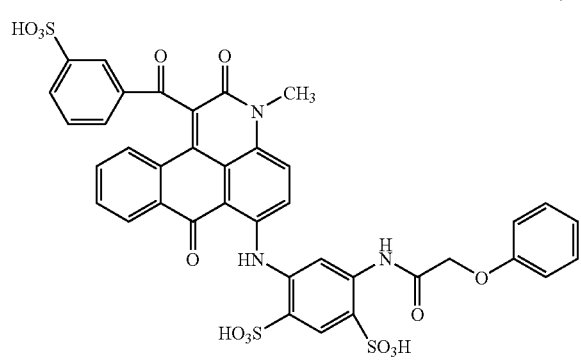

(33)

Examples 21 and 22

(A) Preparation of Ink

Using the compound represented by the formula (16) obtained in the above Example 2, a liquid (ink composition) according to the composition shown in Table 2 described below was prepared and filtered using a 0.45 μm membrane filter to obtain a water-based ink composition for inkjet recording of the present invention. As "water" in Table 2, ion-exchanged water was used, including water for diluting ammonia water. In this regard, water and a 2.8% ammonia water solution were added to adjust the pH of the ink composition to 8 to 10 and to make the total amount 100 parts.

Next, in the same manner as the above except for using the compound represented by the formula (15) obtained in Example 1 (4), an ink composition was obtained. These are respectively Examples 21 and 22. Using these ink compositions, inkjet recording was performed and the recorded images were evaluated. The results are shown in Table 3 described below. In addition, the results of tests on various fastnesses of the recorded image obtained in Example 21 are shown in Table 4.

TABLE 2

| (Ink composition) | |
|---|---|
| The compound of Example 2 (Compound Example No. 2) | 6.0 parts |
| Glycerine | 5.0 parts |
| Urea | 5.0 parts |
| N-Methyl-2-pyrrolidone | 4.0 parts |
| Isopropylalcohol | 3.0 parts |
| Butyl carbitol | 2.0 parts |
| Surfynol 104PG50 (manufactured by Nissin Chemical Industry Co., Ltd.) | 0.1 part |
| Water + 2.8% ammonia water | 74.9 parts |
| Total | 100.0 parts |

Comparative Example 1

For comparison, in the same manner as in Example 21 except for using a compound of the following formula (34) disclosed in Example 7 (Compound No. 36) of Patent Literature 1, an ink composition of Comparative Example 1 was prepared, inkjet recording was performed, and evaluation and tests on various fastnesses of the recorded images were conducted. The results are shown in Tables 3 and 4 described below.

Formula (34)

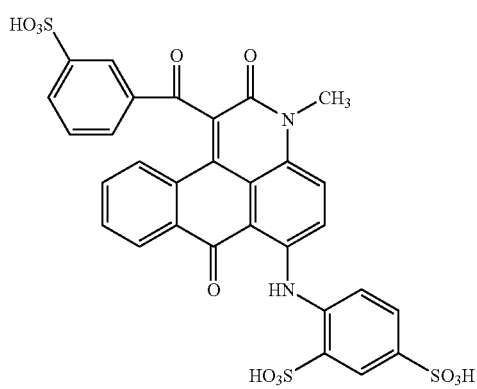

(34)

Comparative Example 2

For comparison, in the same manner as in Example 21 except for using the known compound of the above formula (14) obtained in the above Example 1 (3), an ink composition of Comparative Example 2 was prepared, inkjet recording was performed, and evaluation and tests on various fastnesses of the recorded images were conducted. The results are shown in Tables 3 and 4 described below.

(B) Inkjet Printing

Using an inkjet printer (Pixus iP4100, manufactured by Canon Inc.), inkjet recording was performed on two kinds of glossy paper having an ink image receiving layer containing a porous white inorganic substance. In inkjet recording, an image pattern was made so as to obtain several gradations of print density, and printed matters are produced. In this regard, the kinds of glossy paper are as follows.

Glossy paper 1: trade name: Professional Photo Paper PR-101, manufactured by Canon Inc.

Glossy paper 2: trade name: CRISPIA, manufactured by Seiko-Epson Corporation.

Glossy paper 3: trade name: Advanced Photo Paper, manufactured by Hewlett Packard.

(C) Evaluation of Recorded image

1. Hue Evaluation 1-1. Hue Evaluation on Glossy Paper

Hue and vividness of recorded image: the recorded paper having a print density (D value) of around 1.7 was measured using a colorimetric system (GRETAG SPM50: manufactured by GRETAGMACBETH AG), $L^*$, $a^*$ and $b^*$ values were determined, and vividness $C^*=((a^*)^2+(b^*)^2)^{1/2}$ was calculated from chromaticities ($a^*$ and $b^*$). Hue evaluation was conducted by comparing a sample of Japan Color Standard Magenta from JNC (Japan Printing Machinery Manufacturers Association).

The results of hues of Examples 21 and 22 are shown in Table 3. In this regard, the paper used for Japan Color Standard Magenta is Japan Color Standard Paper.

TABLE 3

| | Hue | | | Vividness |
|---|---|---|---|---|
| | $L^*$ | $a^*$ | $b^*$ | $C^*$ |
| JNC Standard Magenta | 46.3 | 74.4 | −4.8 | 74.6 |
| Glossy paper 1 | | | | |
| Example 21 | 38.5 | 79.3 | −22.9 | 82.5 |
| Example 22 | 39.5 | 80.7 | −18.8 | 82.9 |
| Comparative Example 1 | 36.4 | 79.7 | −21.6 | 82.4 |
| Comparative Example 2 | 32.1 | 75.0 | −33.7 | 82.2 |
| Glossy paper 2 | | | | |
| Example 21 | 37.7 | 81.0 | −27.0 | 85.4 |
| Example 22 | 37.6 | 82.0 | −23.5 | 85.3 |
| Comparative Example 1 | 34.5 | 80.7 | −24.6 | 84.4 |
| Comparative Example 2 | 31.2 | 78.6 | −35.5 | 86.2 |
| Glossy paper 3 | | | | |
| Example 21 | 36.9 | 76.8 | −25.4 | 80.9 |
| Example 22 | 39.1 | 80.1 | −21.3 | 82.8 |
| Comparative Example 1 | 35.1 | 78.1 | −23.2 | 81.5 |
| Comparative Example 2 | 30.5 | 80.1 | −21.3 | 82.8 |

Judging from Table 3, Examples and Comparative Example 1 has an approximate hue to JNC Standard Magenta on any glossy paper, and are thus suitable compounds as a magenta coloring matter for inkjet. In addition, it is also found that $C^*$ values thereof are higher than the value of JNC Standard Magenta and thus the hues thereof have a very high vividness.

It is found that $b^*$ value of Comparative Example 2 is smaller than those of Examples and Comparative Example 1 on any glossy paper and thus the hue thereof is blue-tinged.

From the above results, it is said that the recorded images with the ink composition using the coloring matter of the present invention has JNC Standard Magenta hue and therefore the anthrapyridone compound of the present invention is suitable as a magenta coloring matter for inkjet.

(D) Xenon Light Fastness Test of Recorded Image

Using Atras weatherometer (Ci4100) [manufactured by Toyo Seiki Seisaku-sho, LTD.], each test piece made by printing on glossy papers 1, 2 and 3 was placed, an air space and a soda-lime glass having a thickness of 2 mm were provided in front of each test piece, and irradiation was conducted at an irradiance of 0.36 kw/m², a humidity of 60% RH and a temperature of 24° C. for 100 hours. D value of the part which had had D value of around 1.2 was measured before and after the test, the residual rate was calculated from "before/after test× 100=residual rate (%)" and evaluation was conducted.

The results are shown in Table 4.

(E) Ozone Gas Fastness Test of Recorded Image

Using an ozone weatherometer (manufactured by Suga Test Instruments Co., Ltd.), each test piece made by printing on glossy papers 1, 2 and 3 was left for 24 hours under the circumstances of an ozone concentration of 10 ppm, a humidity of 60% RH and a temperature of 24° C. D value of the part which had had D value of around 1.2 was measured before and after the test, the residual rate was calculated from "before/after test×100=residual rate (%)" and evaluation was conducted.

The results are shown in following Table 4.

(F) Moisture fastness test of recorded image

Using a thermo-hygrostat (manufactured by Ohken Co., Ltd), a test piece made by printing on glossy papers 1~3 was left for 168 hours at 30° C. and 80% RH. The bleeding property of the part which had had D value of around 1.7 was judged by visual observation before and after the test, and evaluation was conducted on a 3 grade scale.

○: No bleeding is observed.

Δ: Slight bleeding is observed.

X: Large bleeding is observed.

The results are shown in following Table 4.

TABLE 4

|  | Light fastness | Ozone fastness | Moisture fastness |
|---|---|---|---|
| Glossy paper 1 |  |  |  |
| Example 21 | 92.6 | 95.0 | ○ |
| Comparative Example 1 | 88.5 | 89.6 | X |
| Comparative Example 2 | 62.1 | 57.5 | X |
| Glossy paper 2 |  |  |  |
| Example 21 | 93.0 | 90.4 | Δ |
| Comparative Example 1 | 88.4 | 88.4 | X |
| Comparative Example 2 | 41.0 | 48.7 | X |
| glossy paper 3 |  |  |  |
| Example 21 | 97.4 | 89.7 | ○ |
| Comparative Example 1 | 93.2 | 86.4 | X |
| Comparative Example 2 | 44.9 | 48.7 | X |

From Table 4, it is found that Example 21 in the light fastness test has a residual rate of 92.6 on glossy paper 1, while Comparative Examples 1 and 2 have smaller values, respectively 88.5 and 62.1 and thus have more color fading than Example 21.

In addition, it is found that in the case of using glossy paper 2, Example 21 has a residual rate of 93.0, while Comparative Examples 1 and 2 have very smaller values, respectively 88.4 and 41.0, and thus have more color fading than Example 21.

It is found that even in the case of using glossy paper 3, Example 21 has a residual rate of 97.4, while Comparative Examples 1 and 2 have very large values, respectively 93.2 and 44.9, and thus have more color fading than Example 21. From the above results, Example 21 has a more excellent light fastness than Comparative Examples 1 and 2 on all the glossy paper.

It is found that in the case of using glossy paper 1 in ozone fastness test, Example 21 has a residual rate of 95.0 while Comparative Examples 1 and 2 have smaller values, respectively 89.6 and 57.5, and thus have more color fading.

It is found that even in the case of using glossy paper 2, Example 21 has a residual rate of 90.4, while Comparative Examples 1 and 2 have smaller values, respectively 88.4 and 48.7 and thus have more color fading.

It is found that even in the case of using glossy paper 3, Example 21 has a residual rate of 89.7, while Comparative Examples 1 and 2 have smaller values, respectively 86.4 and 48.7, and thus have more color fading.

From the above results, Example 21 has more excellent ozone fastness than Comparative Examples 1 and 2.

In moisture fastness test, Example 21 has less bleeding than Comparative Examples 1 and 2 on all the glossy papers, and thus has better moisture fastness.

Example 21 has excellent results in the tests, so it can be said to be very suitable for magenta coloring matter for inkjet.

In addition, the light and ozone fastnesses of the recorded image obtained in Example 22 are also excellent, and nearly equal or more excellent compared to Comparative Example 1.

From the above results, it is clear that the anthrapyridone compound of the present invention is a coloring matter which allows images having even fastnesses, and it can be said that it is extremely excellent as a magenta coloring matter for inkjet in this view.

INDUSTRIAL APPLICABILITY

The anthrapyridone compound of the present invention has high fastnesses and is suitably used as a magenta coloring matter particularly for inkjet printing.

The invention claimed is:

1. An anthrapyridone compound represented by the following formula (1) or a salt thereof:

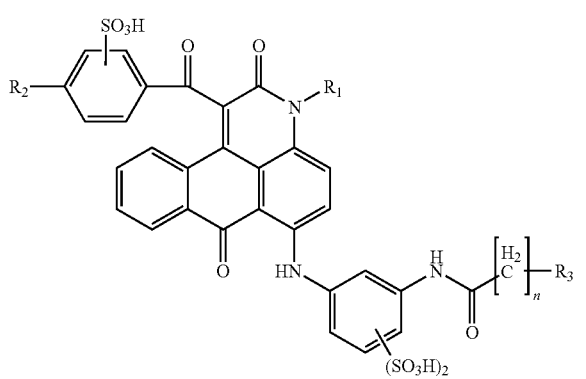

wherein, n represents an integer number of 1 to 3, $R_1$ represents a hydrogen atom, an alkyl group, a hydroxy lower alkyl group, a cyclohexyl group, a mono- or di-alkylaminoalkyl group, or a cyano lower alkyl group, $R_2$ represents a hydrogen atom or a methoxy group, and $R_3$ represents an unsubstituted anilino group or an anilino group having, as a substituent, at least one group selected from the group consisting of a sulfo group, a carboxy group, an alkoxy group, a carbamoyl group, a cyano group, an alkyl group, an anilino group, a phenoxy group, an amino group, a hydroxy group and a mercapto group;

an unsubstituted mono- or di-alkylamino group or a mono- or di-alkylamino group having, as substituent, at least one group selected from the group consisting of a sulfo group, a carboxy group, an alkoxy group, a carbonyl group, a carbamoyl group, a cyano group, an anilino group, a phenoxy group, an amino group, a monoalkylamino group, a dialkylamino group, a hydroxy group, a mercapto group and a phenyl group;

an unsubstituted phenylthio group or a phenylthio group having, as a substituent, at least one group selected from the group consisting of a sulfo group, a carboxy group, an alkoxy group, a carbonyl group, a carbamoyl group, a cyano group, an alkyl group, an anilino group, a phenoxy group, an amino group, a hydroxy group and a mercapto group;

an unsubstituted alkylthio group or an alkylthio group having, as a substituent, at least one group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group;

a naphthylamino group substituted by a sulfo group or an unsubstituted naphthylamino group;

an unsubstituted phenoxy group or a phenoxy group having, as a substituent, at least one group selected from the group consisting of a sulfo group, a carboxy group, an acetylamino group, an amino group, a hydroxy group, a phenoxy group and a phenyl group;

a hydroxy group; a mercapto group; or an unsubstituted amino group; respectively.

2. The anthrapyridone compound or a salt thereof according to claim 1, which is represented by the following formula (2):

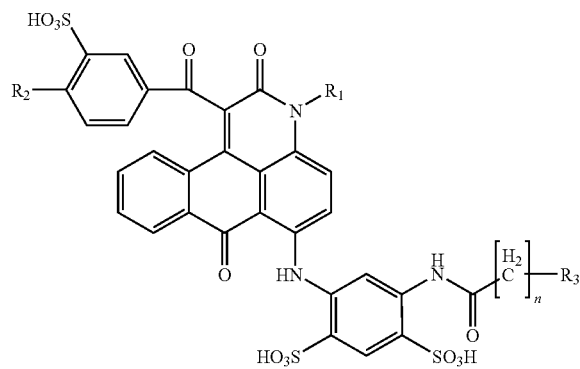

wherein, n, $R_1$, $R_2$ and $R_3$ have the same meanings as in the formula (1).

3. The anthrapyridone compound or a salt thereof according to claim 1, which is represented by the following formula (3):

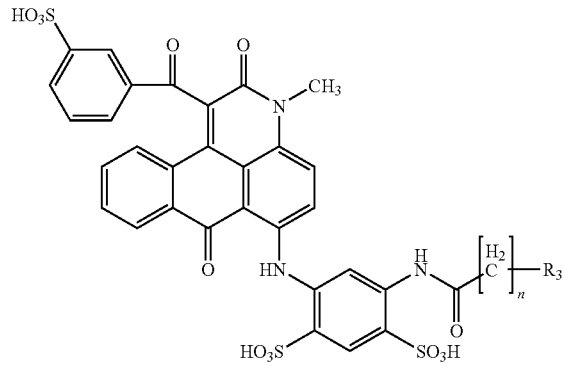

wherein, n and $R_3$ have the same meanings as in the formula (1).

4. The anthrapyridone compound or a salt thereof according to claim 3 wherein:

n is an integer number 1 or 2, $R_3$ is an unsubstituted anilino group or an anilino group having, as a substituent, at least one group selected from the group consisting of a sulfo group, a carboxy group, a C1 to C4 alkoxy group, a C1 to C4 alkyl group, an anilino group, a phenoxy group and an amino group;

an unsubstituted mono- or di-C1 to C10 alkylamino group or a mono- or di-C1 to C10 alkylamino group having, as a substituent, at least one group selected from the group consisting of a sulfo group, a carboxy group, a C1 to C4 alkoxy group, an anilino group, a phenoxy group, an amino group, a phenyl group and a hydroxy group;

an unsubstituted phenylthio group or a phenylthio group having, as a substituent, at least one group selected from the group consisting of a sulfo group, a carboxy group, a C1 to C4 alkoxy group, a C1 to C4 alkyl group, an anilino group, a phenoxy group and an amino group;

an unsubstituted alkylthio group or a C1 to C10 alkylthio group having, as a substituent, at least one group selected from the group consisting of a sulfo group, a carboxy group, a C1 to C4 alkoxy group, an anilino group, a phenoxy group and an amino group;

a naphthylamino group substituted by a sulfo group or an unsubstituted naphthylamino group;

an unsubstituted phenoxy group or a phenoxy group having, as a substituent, at least one group selected from the group consisting of a sulfo group, a carboxy group, an acetylamino group, an amino group, a hydroxy group, a phenoxy group and a phenyl group; or a mono- or di-C1 to C4 alkylamino C1 to C4 alkylamino group;

a hydroxy group; a mercapto group; or an amino group.

5. The anthrapyridone compound or a salt thereof according to claim 4, wherein $R_3$ is an unsubstituted anilino group or an anilino group having, as a substituent, a sulfo group or a carboxy group; an unsubstituted mono-C1 to C10 alkylamino group or a mono-C1 to C10 alkylamino group having, as a substituent, a sulfo group, a carboxy group or a phenyl group; an unsubstituted di-C1 to C6 alkylamino group; a phenylthio group substituted by a carboxy group; an unsubstituted C1 to C10 alkylthio group or a C1 to C10 alkylthio group having, as a substituent, a carboxy group or an amino group; or an unsubstituted di-C1 to C4 alkylamino C1 to C4 alkylamino group.

6. The anthrapyridone compound or a salt thereof according to claim 4, wherein $R_3$ is an unsubstituted anilino group or an anilino group having, as a substituent, a carboxy group; an unsubstituted mono-C1 to C8 alkylamino group or a mono-C1 to C8 alkylamino group having, as a substituent, a sulfo group, a carboxy group or a phenyl group; an unsubstituted di-C1 to C6 alkylamino group; a phenoxy group; a phenylthio group substituted by a sulfo group or a carboxy group; a C1 to C10 alkylthio group substituted by a carboxy group or an unsubstituted C1 to C10 alkylthio group.

7. An ink composition comprising the anthrapyridone compound or a salt thereof according to claim 1.

8. An ink composition, which contains water, a water-soluble organic solvent and the anthrapyridone compound or a salt thereof according to any one of claims 1 to 6.

9. The ink composition according to claim 7, wherein the content of an inorganic impurity in said compound is 1% by mass or less relative to the total mass of said anthrapyridone compound or a salt thereof which is contained in said ink composition as a coloring matter.

10. The ink composition according to claim 7, wherein the content of said anthrapyridone compound or a salt thereof which is contained in said ink composition as a coloring matter is 0.1 to 20% by mass relative to the total mass of the ink composition.

11. The ink composition according to claim 7, which is for inkjet recording.

12. An inkjet recording method comprising discharging ink droplets of the ink composition according to claim 11 in response to a recording signal for recording on a record-receiving material.

13. The inkjet recording method according to claim 12, wherein the record-receiving material is a communication sheet.

14. The inkjet recording method according to claim 13, wherein the communication sheet has an ink image receiving layer containing a porous white inorganic substance.

15. A colored product which is colored with the ink composition according to claims 7.

16. The colored product according to claim 15, which coloring is conducted by an inkjet printer.

17. An inkjet printer which comprises a container containing the ink composition according to claim 7.

18. An anthrapyridone compound represented by the following formula (4) or a salt thereof:

(4)

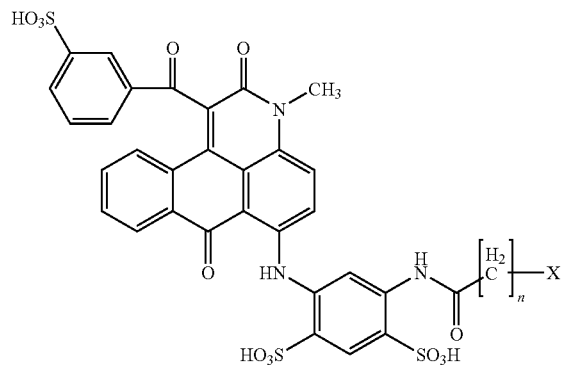

wherein, n represents an integer number of 1 to 3 and X represents a leaving group.

19. The anthrapyridone compound or a salt thereof according to claim 18, wherein n is an integer number of 1 or 2, and X is a chlorine atom, a bromine atom or an iodine atom.

20. The anthrapyridone compound or a salt thereof according to any one of claims 1 to 3, wherein n is an integer number of 1 or 2 and $R_3$ is a carboxy-substituted C3 to C8 alkylamino group.

21. A method for producing an anthrapyridone compound represented by the following formula (1) or a salt thereof:

(1)

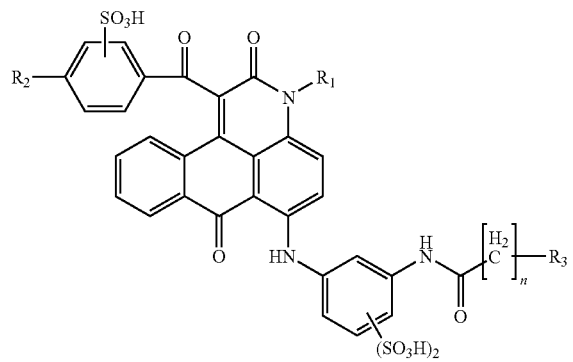

wherein n represents an integer number of 1 to 3, $R_1$ represents a hydrogen atom, an alkyl group, a hydroxy lower alkyl group, a cyclohexyl group, a mono- or di-alkylaminoalkyl group, or a cyano lower alkyl group, $R_2$ represents a hydrogen atom or a methoxy group, and $R_3$ represents an unsubstituted anilino group or an anilino group having, as a substituent, at least one group selected from the group consisting of a sulfo group, a carboxy group, an alkoxy group, a carbamoyl group, a cyano group, an alkyl group, an anilino group, a phenoxy group, an amino group, a hydroxy group and a mercapto group; an unsubstituted mono- or di-alkylamino group or a mono- or dialkylamino group having, as a substituent, at least one group selected from the group consisting of a sulfo group, a carboxy group, an alkoxy group, a carbonyl group, a carbamoyl group, a cyano group, an anilino group, a phenoxy group, an amino group, a monoalkylamino group, a dialkylamino group, a hydroxy group, a mercapto group and a phenyl group; an unsubstituted phenylthio group or a phenylthio group having, as a substituent, at least one group selected from the group consisting of a sulfo group, a carboxy group, an alkoxy group, a carbonyl group, a carbamoyl group, a cyano group, an alkyl group, an anilino group, a phenoxy group, an amino group, a hydroxy group and a mercapto group; an unsubstituted alkylthio group or an alkylthio group having, as a substituent, at least one group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group; a naphthylamino group substituted by a sulfo group or an unsubstituted naphthylamino group; an unsubstituted phenoxy group or a phenoxy group having, as a substituent, at least one group selected from the group consisting of a sulfo group, a carboxy group, an acetylamino group, an amino group, a hydroxy group a phenoxy group and a phenyl group; a hydroxy group; a mercapto group; or an unsubstituted amino group; respectively comprising reacting an anthrapyridone compound represented by the following formula (10):

(10)

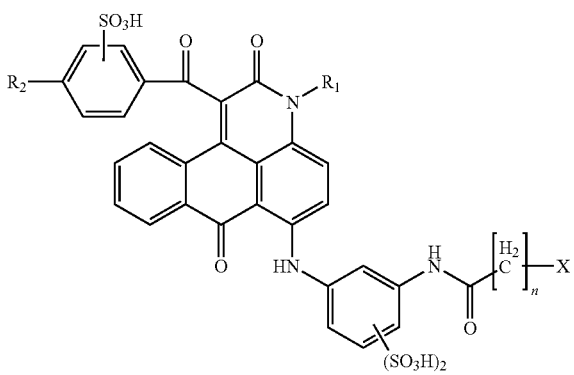

wherein:
n represents an integer number of 1 to 3,
$R_1$ represents a hydrogen atom, an alkyl group, a hydroxy lower alkyl group, a cyclohexyl group, a mono- or di-alkylaminoalkyl group or a cyano lower alkyl group,
$R_2$ represents a hydrogen atom or a methoxy group, and X represents a leaving group
or a salt thereof with a compound represented by
Formula $R_3$—H
wherein, $R_3$ represents;
an unsubstituted anilino group or an anilino group having, as a substituent, a group selected from the group consisting of a sulfo group, a carboxy group, an alkoxy group, a carbamoyl group, a cyano group, an alkyl group, an anilino group, a phenoxy group, an amino group, a hydroxy group and a mercapto group;
an unsubstituted mono- or di-alkylamino group or a mono- or di-alkylamino group having, as a substituent, a group selected from the group consisting of a sulfo group, a carboxy group, an alkoxy group, a carbonyl group, a carbamoyl group, a cyano group, an anilino group, a phenoxy group, an amino group, a monoalkylamino group, a dialkylamino group, a hydroxy group, a mercapto group and a phenyl group;
an unsubstituted phenylthio group or a phenylthio group having, as a substituent, a group selected from the group consisting of a sulfo group, a carboxy group, an alkoxy group, a carbonyl group, a carbamoyl group, a cyano group, an alkyl group, an anilino group, a phenoxy group, an amino group, a hydroxy group and a mercapto group;
an unsubstituted alkylthio group or an alkylthio group having, as a substituent, a group selected from the group consisting of a sulfo group, a carboxy group, an alkoxy group, a carbonyl group, a carbamoyl group, a cyano group, an anilino group, a phenoxy group, an amino group, a hydroxy group, a mercapto group and a phenyl group;
a naphthylamino group substituted by a sulfo group or an unsubstituted naphthylamino group;
an unsubstituted phenoxy group or a phenoxy group having, as a substituent, a group selected from the group consisting of a sulfo group, a carboxy group, an acetylamino group, an amino group, a hydroxy group, a phenoxy group and a phenyl group;
a hydroxy group; a mercapto group; or an unsubstituted amino group.

22. An anthrapyridone compound represented by the following formula (113) or a salt thereof:

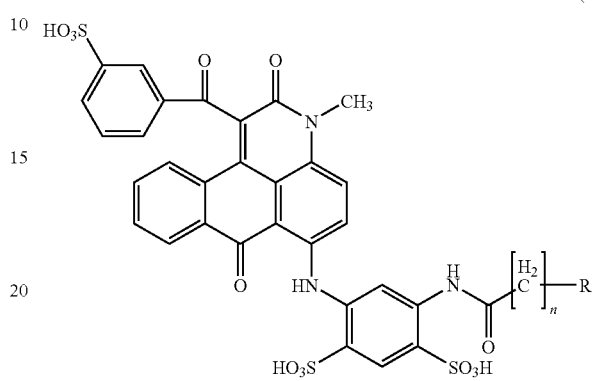

(113)

wherein, n represents an integer number of 1 to 3, and
R represents an unsubstituted anilino group or an anilino group having, as a substituent, a carboxy group; an unsubstituted mono-C1 to C10 alkylamino group or a mono-C1 to C8 alkylamino group having, as a substituent, a sulfo group, a carboxy group or a phenyl group; an unsubstituted di-C1 to C6 alkylamino group; a phenoxy group; a phenylthio group substituted by a sulfo group or a carboxy group; a C1 to C10 alkylthio group substituted by a carboxy group or an unsubstituted C1 to C10 alkylthio group; or a halogen atom.

* * * * *